United States Patent [19]

Moorehead

[11] Patent Number: 5,147,332

[45] Date of Patent: Sep. 15, 1992

[54] MULTI-VALVE CATHETER FOR IMPROVED RELIABILITY

[75] Inventor: H. Robert Moorehead, Salt Lake City, Utah

[73] Assignee: C.R. Bard, Inc., Murrah Hill, N.J.

[21] Appl. No.: 702,032

[22] Filed: May 17, 1991

[51] Int. Cl.$^5$ .............................................. A61M 5/00
[52] U.S. Cl. ..................................... 604/247; 604/280
[58] Field of Search ............... 604/264, 247, 280, 281, 604/282, 283, 284, 164, 168, 43, 44, 45

[56] References Cited

U.S. PATENT DOCUMENTS

| | | | |
|---|---|---|---|
| 3,020,913 | 2/1962 | Heyer | 128/350 |
| 3,042,045 | 7/1962 | Sheridan | 128/349 |
| 3,111,125 | 11/1963 | Schulte | 128/350 |
| 3,217,710 | 11/1965 | Beall et al. | 128/214 |
| 3,769,982 | 11/1973 | Schulte | 128/350 |
| 3,885,561 | 5/1975 | Cami | 128/214 |
| 4,327,722 | 5/1982 | Groshong et al. | 128/214.4 |
| 4,549,879 | 10/1985 | Groshong et al. | 604/247 |
| 4,657,536 | 4/1987 | Dorman | 604/247 |
| 4,671,796 | 6/1987 | Groshong et al. | 604/247 |
| 4,701,166 | 10/1987 | Groshong et al. | 604/247 |
| 4,737,152 | 4/1988 | Alchas | 604/256 |
| 4,753,640 | 6/1988 | Nichols et al. | 604/247 |
| 4,973,319 | 11/1990 | Melsky | 604/247 |
| 4,995,863 | 2/1991 | Nichols et al. | 604/247 |

Primary Examiner—John D. Yasko
Attorney, Agent, or Firm—Workman, Nydegger & Jensen

[57] ABSTRACT

A novel apparatus for a catheter for use in aspirating and/or infusing fluids into a patient. The catheter, having a proximal end and a distal end, comprises a plurality of valves in the walls of the catheter comprised of relatively soft material while maintaining a predetermined degree of structural integrity at the catheter tip. The plurality of valves are radially distributed in offset relation around the distal end of the catheter such that no two valves lie in any one radial plane. Similarly, the plurality of valves are longitudinally separated or offset in their placement at relatively short, but differentiated, distances from the distal end of the catheter such that no two valves lie in any one axial plane. The radial and longitudinal separation of the valves helps avoid structural weakness in the catheter, particularly at the distal end of the catheter. The catheter may be a single-lumen catheter, or a multi-lumen catheter.

The plurality of valves are comprised of a primary valve constructed to be preferably operable during infusion and/or aspiration, and at least one secondary valve which operates as a surrogate should the primary valve become partially or totally occluded. The catheter enables repeated infusion and/or aspiration over a period of time.

The present invention also includes methods for using and manufacturing the catheter by following certain steps.

95 Claims, 8 Drawing Sheets

MULTI-VALVE CATHETER FOR IMPROVED RELIABILITY

BACKGROUND

1. The Field of the Invention

The present invention relates to methods and apparatus for a catheter provided with a plurality of valves in a single lumen, the valves comprised of linearly extending slits through the catheter wall. In particular, the preferred embodiment of the invention relates to methods and apparatus for intravascular catheters provided with a pair of axially and longitudinally displaced two-way, three-positioned slit valves, one of the pair of valves preferably opening to aspirate or infuse at a predetermined pressure differential applied to the catheter lumen, the second of the pair of valves acting as a surrogate to the first valve should the first valve fail to operate properly.

2. The Background Art

The aspiration and infusion of fluids to a patient's body through a catheter is vital to the patient's well-being. The deprivation of necessary body fluids, medicines, and the like can result in severe damage to a patient's health. Therefore, the most efficient and safe way to aspirate or infuse fluids into a patient through a catheter is an area which requires close attention.

An essential feature characterized by all catheters employed for aspiration or infusion purposes is some type of opening through which fluids may travel. Because of the tubular connecting structure of catheters, such an opening is provided by the inner lumen of the catheters which can usually be accessed at the distal and proximal ends of the catheter. The opening allows fluids surrounding the catheter to be aspirated, and the opening allows medical personnel to infuse fluids through the opening to the same areas that may be aspirated.

The desirability of employing such an opening, however, is lessened due to the continual communication between the catheter and the body cavity of the patient. At some points, such as the withdrawal of blood, it is necessary to bar the flow of fluids to or from a patient. Although physically clamping the catheter to prevent fluid flow therein is possible, the physical manipulations necessary are undesirable due to the constant attention the clamping and unclamping would require. In addition, the physical manipulations are undesirable because of the weakening and wear which would be caused on the catheter.

Recently, those in the art have proposed placement of a valve in the wall of a catheter to bar the flow of fluids to or from a patient through the catheter. The valve, preferably a slit valve formed in the wall of the catheter, usually remains in a closed position with adjacent edges of the valve (e.g., slit) abutting each other. Nevertheless, the adjacent edges may separate in response to a predetermined pressure differential, thus permitting fluid flow through the catheter.

If a predetermined positive pressure differential between the inside and outside of the catheter is exceeded, fluids travel down the catheter lumen, from the inside of the catheter lumen, through the valve to the patient. If a predetermined negative pressure differential between the inside of the catheter is exceeded, fluids travel from the patient to the catheter.

The placement of a slit valve in the wall of the catheter, however, risks the loss of the structural integrity of the catheter. A slit valve increases the flexibility and movement of the catheter wall. The loss of structural integrity is magnified by the number of slit valves placed in the wall of the catheter.

As a result of this loss of structural integrity, catheters containing more than one slit valve were unable to maintain the required degree of catheter tip structural integrity. The increase in the number of slit valves increased the flexibility and movement of the wall of the catheter, and the combination of a number of slit valves has led to the collapse of catheters. Such collapse of catheters prevents aspiration or infusion of fluids from the catheter through the valve.

The collapse of a catheter upon itself, and other catheter-related problems, may seem correctable due to the temporary nature of some catheters. Nevertheless, some catheters, such as long-term indwelling catheters, may potentially be implanted in a patient for several months or years. Simple structural flaws in such catheters can cause unique problems to those particular types of patients using these catheters where it is critical to consistently keep the catheters operating for the well-being of the patient.

Since the introduction of catheters containing multi-position-type slit valves, a relatively low, but constant, level of adverse comments have been received from users about the reliability of these slit valves. During infusion, the lips of the slit valve open outwardly into the blood vessel of the patient permitting fluid to flow through the catheter and into the blood vessel. While functioning successfully to transmit fluids into the body of the patient, unless the slit valve is placed at the most distal point of the catheter, an area exists at the end of the catheter which cannot be cleared of infused liquid. This "dead space" may be an area where a clot may form and/or microorganisms may grow and become a source of contamination; hence, to avoid dead space, the location for placing the valves in the wall of a catheter is severely limited.

Difficulty has also been reported in that multi-position valves may not be able to function consistently for aspiration purposes, particularly when the catheter has been implanted for a long period of time. There are two likely explanations for the cause of such partial dysfunction. A thrombus may have formed over or adjacent to the single slit valve. This could impede the inward opening of the slit valve lips, while enabling them to open outwardly.

An alternative situation is that the side of the catheter in which the slit valve is formed may occasionally come to rest against or in close proximity to the wall of the blood vessel in which the catheter tip is disposed. Under such conditions, any attempt to draw blood inwardly through the slit valve draws the catheter against the wall of the blood vessel, thereby preventing free aspiration. Under such circumstances, infusion would remain unaffected.

Blockage of the multi-position valves can lead to problems other than the prevention of free aspiration. Some medical personnel may attempt to dislodge the catheter from the blocking surface by increasing the pressure on the lumen of the catheter. Such attempts can potentially cause damage to the tissues adjacent the blocking surface which are susceptible to pressure differentials.

In any event, blockage of the multi-position valves, or the incidence of infection caused by contamination of the dead space, usually requires the replacement of the catheter from catheter technology allows medical personnel to replace catheters that have become obstructed or contaminated, such a result is impractical. Unnecessary time and energy spent replacing catheters, not to mention the discomfort experienced by patients during catheter replacement, are problems which should have been compensated for by catheters available according to current existing standard practices.

A need, therefore, exists in the art for a catheter having a plurality of valves, at least one of the valves preferably operating during infusion or aspiration, but the others capable of operating, or acting as a surrogate, should the preferred valve become occluded.

Also, a need exists in the art for a catheter having a plurality of valves that allows preferred operation of a distal valve in relation to any proximal valves during infusion and flushing to minimize the remainder of infused fluids in the lumen of the catheter.

Additionally, a need exists in the art for a catheter having a plurality of valves such that the valves are located so as not to destroy the structural integrity of the catheter, particularly at the distal end of the catheter.

Further, a need exists in the art for a catheter having a plurality of valves which will have the capability of placing and using the catheter without a major deviation from currently existing standard practices.

Still further, a need exists in the art for a catheter having a plurality of valves wherein the plurality of valves operate at the positive and negative pressure differentials applicable in single-valve catheters.

BRIEF SUMMARY AND OBJECTS OF THE INVENTION

The present invention seeks to resolve incidental problems during the infusion or aspiration of fluids through catheters disposed in a patient. More specifically, the apparatus and methods of this invention constitute an important advance in the medical art for biasing the infusion or aspiration of fluids, such as blood, through a primary valve of an intravascular catheter while providing secondary (i.e., surrogate) valves for infusing or aspirating fluids should the primary valve become partially or totally occluded.

One object of the present invention is to provide an apparatus and methods for a catheter having a primary valve that is preferably operated during infusion or aspiration, but having secondary valves which operate should the primary valve become partially or totally occluded.

Also, it is an object of the present invention to provide an apparatus and methods for a catheter having a primary valve that preferably operates in relation to any proximal secondary valves during infusion and flushing to minimize the remainder of infused fluids in the lumen of the catheter.

Additionally, it is an object of the present invention to provide an apparatus and methods for a catheter having a plurality of valves such that the valves are located so as not to destroy the structural integrity of the catheter, particularly at the distal end of the catheter.

Still another object of the present invention is to provide an apparatus and methods for a catheter having a plurality of valves which will have the capacity of placing and using the catheter without a major deviation from currently existing standard practices.

A further object of the present invention to provide an apparatus and methods for a catheter having a plurality of valves wherein the plurality of valves operate at the positive and negative pressure differentials applicable in single-valve catheters.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

To achieve the foregoing objects, and in accordance with the invention as embodied and broadly described herein, the catheter used for the aspiration or infusion of fluids to a patient comprises a cannula having an outer wall made of a biocompatible material with a distal end and a proximal end.

The cannula has at least one internal lumen for transmitting liquids, the at least one lumen providing for two-way fluid flow between the proximal end and the distal end of the cannula. The fluid flow is initiated by the application of a pressure differential to the fluid in the cannula.

The plurality of three-position valves communicating between the at least one lumen of the cannula and the exterior of the cannula have edges which abut each other to prevent fluid flow therethrough. The edges move outwardly from one another when the pressure inside the at least one lumen is greater than the pressure outside the at least one lumen to infuse fluids from the at least one lumen. The edges move inwardly when the pressure outside the at least one lumen is less than the pressure inside the at least one lumen to withdraw fluid from the at least one lumen.

The plurality of valves preferably include a primary valve constructed to be preferably operable during aspiration or infusion. There is at least one secondary valve acting as a surrogate to the primary valve should the primary valve fail to operate. The primary valve is constructed to be preferably operable during aspiration or infusion by mechanical or chemical means. Thus, because of the mechanical or chemical treatment, the primary valve is designed to open at a lower threshold pressure differential than the at least one secondary valve.

The present invention also embodies that the plurality of valves be radially distributed in offset relation around the distal end of the catheter such that no two valves lie in any one radial plane. Similarly, the plurality of valves are longitudinally separated or offset in their placement at relatively short but difficult distances from the distal end of the catheter such that no two valves lie in any one axial plane. The radial and longitudinal separation of the valves helps avoid structural weakness in the catheter, particularly at the distal end of the catheter.

The present invention also comprises methods for using and manufacturing catheters to be employed for the aspiration and infusion of fluids to a patient.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE PREFERRED EMBODIMENTS

Figure 1:
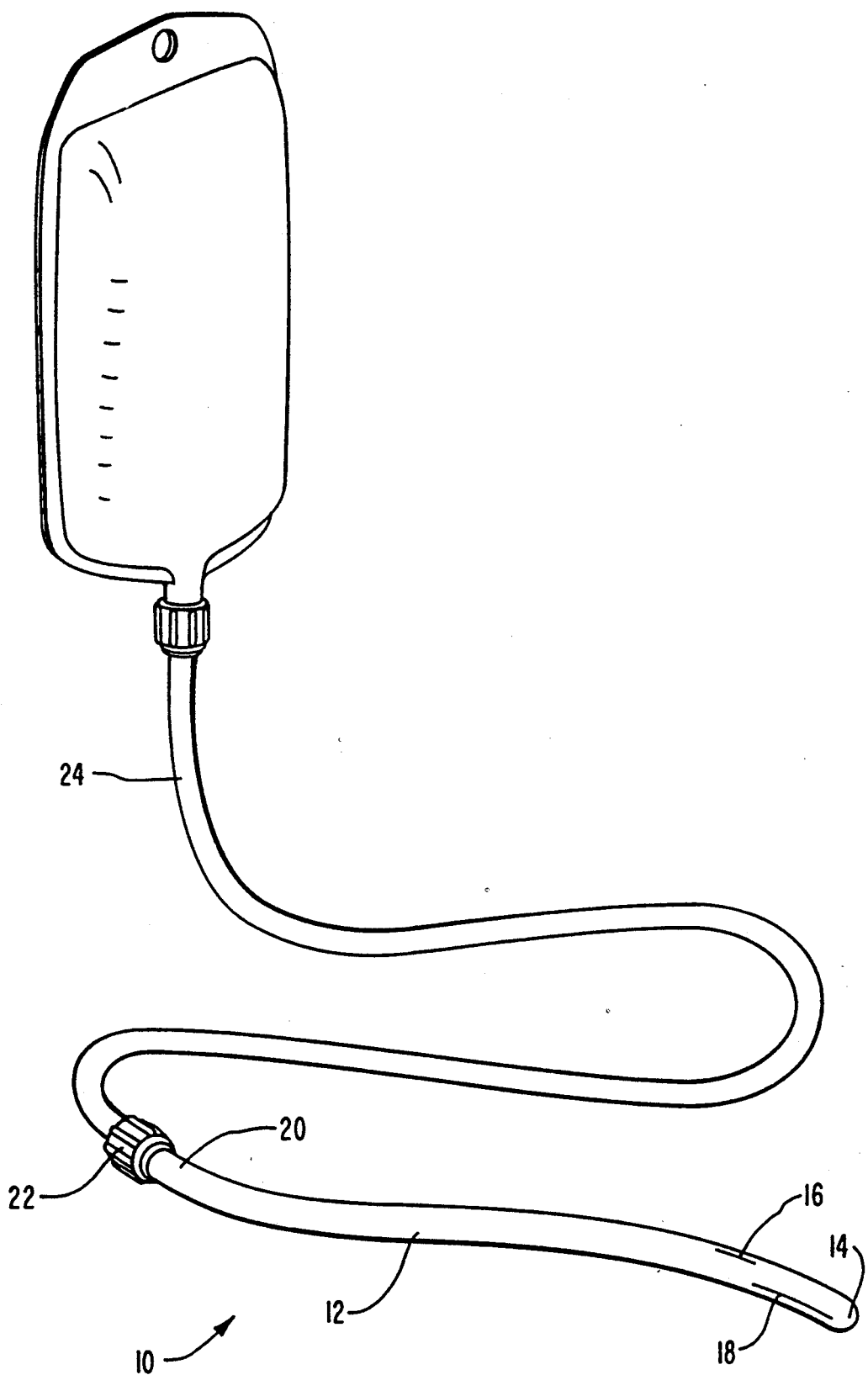
FIG. 1 is a perspective view of the preferred embodiment of the present invention as an apparatus.

The present invention can be best understood by reference to the drawings, wherein like parts are designated with like numerals throughout. The present invention as it pertains to the apparatus can be understood with reference to FIG. 1. FIG. 1 illustrates the apparatus disclosed in the present invention in its preferred embodiment. FIG. 1 represents a perspective view of the device defining therein an improved reliable catheter 10 within the scope of the present invention. Reliable catheter 10 includes a flexible cannula or catheter 12.

Catheter 12 is made of a durable and pliable, yet shape-retaining, synthetic elastomeric material. It is presently preferred that the material comprise an ultra-soft synthetic material. Typically, such material should have a hardness of less than 100 durometers and an elongation percentage of up to 700%. Above all else, the material maintains a predetermined degree of catheter tip rigidity in order to consistently enable infusion and aspiration while maintaining structural integrity. Otherwise catheter 12 would collapse upon itself, and fluid flow through catheter 12 would be prevented.

A preferred material is a silicone rubber tubing having a hardness of about 65±5 durometers sold under the trade name SILASTIC® by Dow Corning Co., Midland, Mich. Catheter 12 is manufactured from a two-part silicone elastomer that consists of dimethyl- and methylvinyl-siloxane copolymers and reinforcing silica. The present invention, however, is not limited to the use of silicone rubber tubing. Tubings made of other materials are possible.

The preferable nature of the materials discussed for the construction of catheter 12 can be characterized by the fact that they assimilate to the environment in which they are placed, specifically the human body. The biocompatibility of the materials is distinguished by (1) their resistance to hardening over time, which could damage surrounding tissues; (2) their resistance to the growth of microbiological substances as possible source of contaminants upon a catheter surface; and (3) their non-bio-reactivity over a long period of time.

Present at the distal end 14 of catheter 12 are at least two valves 16 and 18. The opposite, or proximal end 20, of catheter 12 is terminated by a conventional coupling 22 of a type that is commonly used on medical catheters of this type. The coupling connects to a mating fitting at the end of a connector 24 extending from a source of infusate or it can be connected to the outlet of an implantable port or to a syringe for withdrawing fluids through catheter 12.

Distal end 14 of catheter 12 is closed and rounded. Because catheter 12 is tubular in nature, a cylindrical internal hollow lumen 28 exists at distal end 14 of catheter 12. In manufacturing the preferred embodiment, lumen 28 is closed off by the addition of a liquid silicone adhesive filler that hardens after curing for a period of time. Distal end 14 of catheter 12 is formed in a die to make a round tip during curing. The addition of the filler maintains the structural integrity of distal end 14 of catheter 12 while acting as a seal to close off lumen 28.

Distal end 14 is preferably at least partially radiopaque so that its precise position in the body may be radiologically verified. Also, catheter 12 is preferably transparent at proximal end 20 so that the physician can visually determine the presence of air bubbles, blood, or other liquids in any lumens during and after insertion.

Catheter 12 has cylindrical exterior surface 30 and the previously mentioned lumen 28. A wall layer 32 resides between exterior surface 30 and lumen 28. Lumen 28 allows fluid flow between distal end 14 and proximal end 20 of catheter 12. Fluid flow is most often initiated by applying a pressure differential at proximal end of catheter 12.

Although catheter 12 is illustrated as a single lumen, catheter 12 may comprise more than one liquid transmitting lumen. Where more than one lumen is employed, catheter 12 comprises wall means to define a plurality of independently usable lumens extending substantially the entire length of catheter 12. Wall means include an internal body of material which defines and separates the plurality of lumens. The internal body of material provides internal body and wall structure which provides for separate definition of the plurality of spaced lumens.

Lumen 28 of catheter 12 is cylindrical. Likewise, a catheter comprising a plurality of lumens may include a plurality of cylindrical lumens. Nevertheless, catheter 12 need not be comprised of cylindrical lumens. As an example which is not meant to limit the present invention, catheter 12 may comprise a D-shaped lumen.

The D-shaped lumen in a catheter was first reported by Pat. No. 4,753,640, which prevented occlusion and accommodated continued liquid flow, even when the catheter was inadvertently kinked, bent, twisted or collapsed. That catheter comprised a generally cylindrical catheter formed of a body of elastomeric material defining an outside smooth cylindrical surface and a single D-shaped axial lumen. The lumen included linear wall surfaces. Linear wall surfaces were joined tangentially by a small diameter fillet corner and surfaces and tangentially by a small diameter fillet corner. Linear wall surfaces were joined tangentially by an arcuate wall surface.

In the present invention, the preferred use of catheter 12 is as an intravascular catheter. Nevertheless, catheter 12 is not limited to an intravascular catheter. By way of example and not limitation, catheter 12 may be a peritoneal, intraarterial, gastrointestinal, umbilical, or epidural catheter. The different catheters may vary in size or shape when embodying the principles of the present invention.

The catheters included in the present invention can all be characterized by generally common features. Each has a primary opening that may experience blockage from materials found in the environments surrounding the catheters. The catheters benefit from the provision of a back-up or surrogate opening which would reliably operate were the primary valve to fail to function due to the blockage.

Similarly, each of the catheters seeks to avoid the possibility of contamination which can lead to subsequent infection in a patient. Where the catheter has more than one valve, if a distally located valve remains closed while a more proximal valve opens in response to a pressure differential, a reservoir is created in the lumen of the catheters during infusion and flushing. This reservoir is a source for contaminating fluids. Thus, these catheters benefit by a primary value that preferably operates in relation to any proximal secondary valves during infusion and flushing to minimize the remainder of infused or flushed fluids in the lumen of the catheter and their contaminating effect.

As discussed generally, the invention comprises valving means placed in the wall of catheter 12. Each valving means is defined by a plurality of valves. Each valve is preferably a slit extending through the wall of catheter 12, with the slit being made longitudinally along the axis of catheter 12. Each slit valve is preferably defined by opposed, aligned, normally abutted, parallel edges of oppositely disposed slit wall segments of the wall between the associated lumen and the exterior surface of distal end 14 of catheter 12. Reference to FIG. 1 can be made for further illustration.

In FIG. 1, catheter 12 has two valves 16 and 18, each having opposed aligned abutting wall edges 34, the abutments being engaged in a sealing relationship. Edges 34 are respectively integral with oppositely disposed wall layer 32 of catheter 12. Edges 34 are capable of flexing inwardly or outwardly from their abutted position, responsive to predetermined liquid pressure differentials to thereby relatively rotate edges 34 away from each other into an open-spaced relationship. Where the application of a pressure differential establishes a higher pressure level on the inside of the at least one lumen than the pressure level at the area outside the at least one lumen, a positive pressure differential is said to exist. Where the application of a pressure differential establishes a lower pressure level on the inside of the at least one lumen than the pressure level at the area outside the at least one lumen, a negative pressure differential is said to exist.

Controlled liquid pressure differential between lumen 28 and exterior of distal end 14 of catheter 12 are capable of placing the valves in many positions, preferably three. By applying a predetermined positive pressure to lumen 28, a desired liquid is infused into the vein of a patient by forcing the associated valve to open. By applying a negative pressure to lumen 28, liquid within a body cavity is withdrawn into lumen 28. Under normal physiologic pressures, the valve will remain closed, the edges abutted in a sealing relationship.

Figure 2:
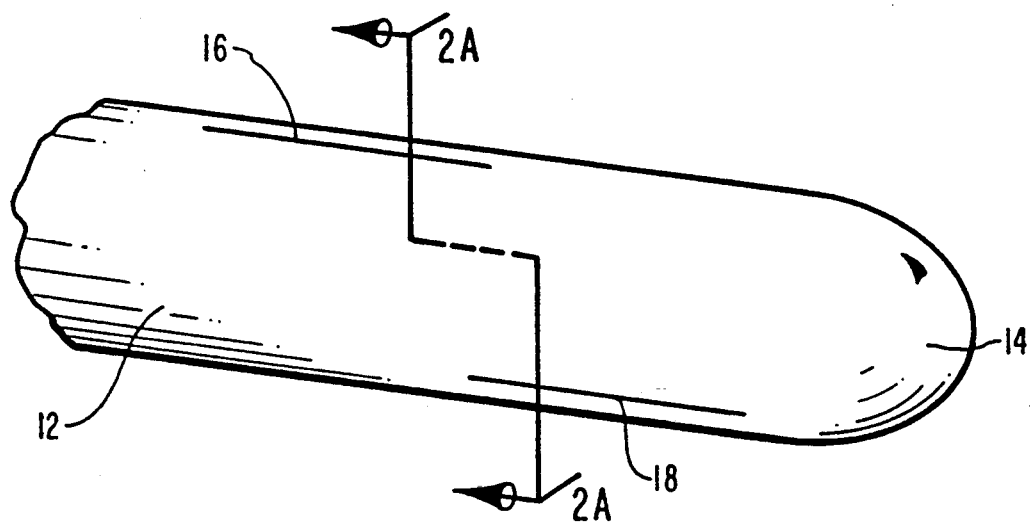
FIG. 2 is a perspective view of the preferred embodiment of the present invention in which both the distal and proximal valves remain in a closed position because they are not subject to threshold pressure differentials.
Figure 3:
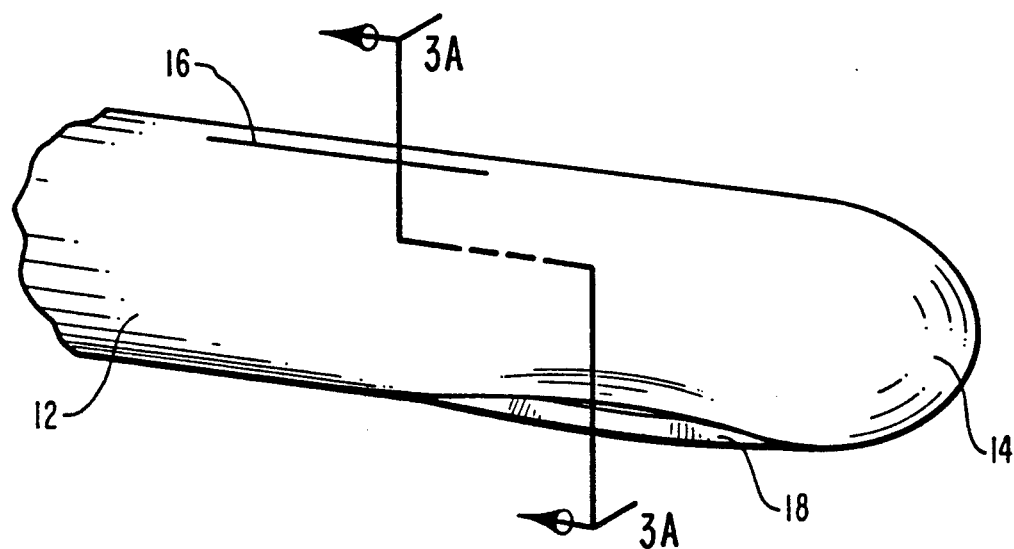
FIG. 3 is a perspective view of the preferred embodiment of the present invention, the distal valve preferably operating to the exclusion of the proximal valve.
Figure 4:
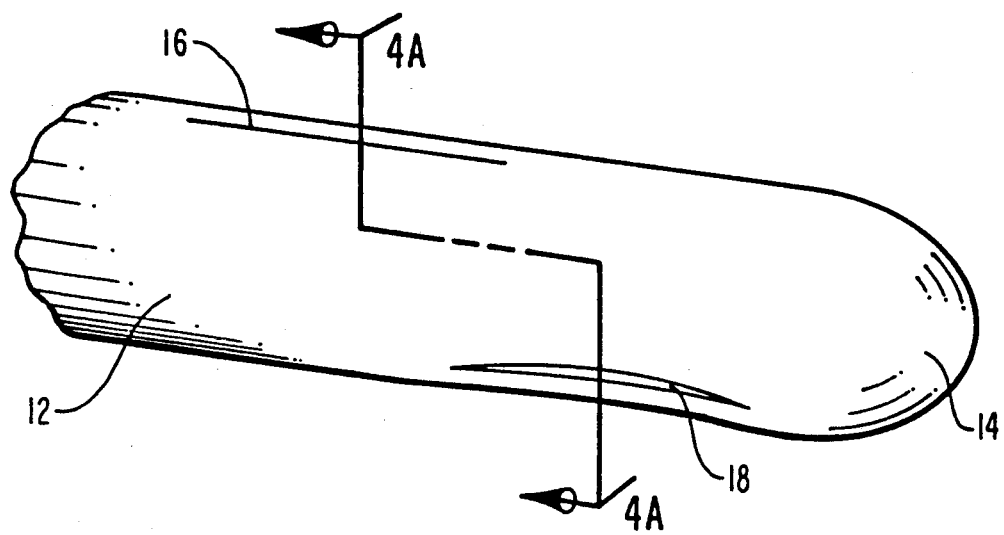
FIG. 4 is a perspective view of the preferred embodiment of the present invention, the distal valve preferably operating to the exclusion of the proximal valve.

In greater detail in FIGS. 2, 3, and 4, the three positions include the normally closed position, where there is not a sufficient pressure differential to separate edges 34 from their abutted relationship. Edges 34 are disposed in opposed aligned abutting relation to engage in a sealing relation in FIG. 2. In the position illustrated in FIG. 3 the outwardly flexed open condition exists where there is a sufficient positive pressure differential that wall segments 36 flex outwardly in an open position to accommodate fluid discharge through the associated lumen to the body cavity in which distal end 14 of catheter 12 is disposed. In the position illustrated in FIG. 4, the inwardly flexed open condition exist where there is a sufficient negative pressure differential that wall segments 36 flex inwardly in an open condition to accommodate fluid flow across the valve from the body cavity in which distal end 14 of catheter 12 is disposed. The slit valve of the present invention automatically returns to the position illustrated in FIG. 2 due to the memory of the material from which it is formed when the pressure differential falls below a predetermined amount.

Figure 2A:
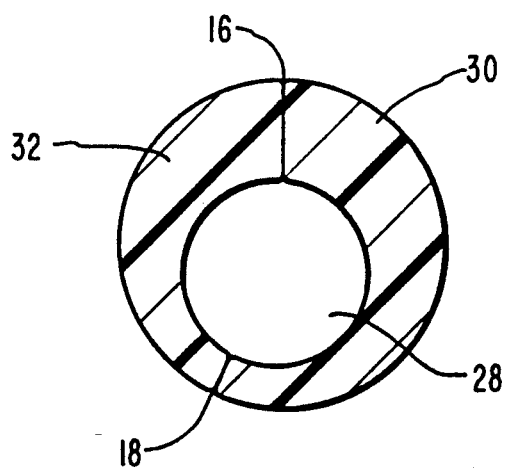
FIG. 2a is a cross-sectional view of the valves of the catheter taken along line 2a of FIG. 2.
Figure 3A:
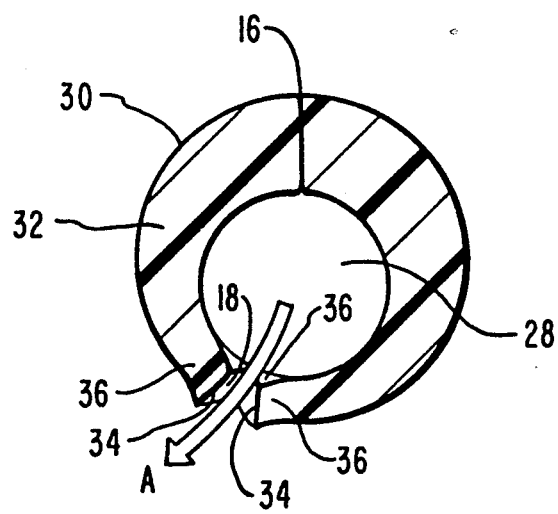
FIG. 3a is a cross-sectional view of the catheter taken along line 3a of FIG. 3, the distal valve in an open outwardly flexed position.
Figure 4A:
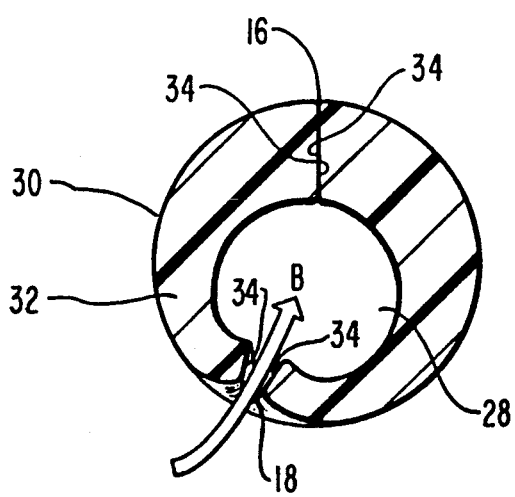
FIG. 4a is a cross-sectional view of the catheter taken along line 4a of FIG. 4, the distal valve in an open inwardly flexed position.

FIGS. 2a, 3a, and 4a show the preferred operation of each three-position slit valve in a cross-sectional view. Upon application of a predetermined pressure differential between the interior and exterior of distal end 14 of catheter 12 reactive to valve 18 but not valve 16, wall segments 36 of valve 18 will deflect or flex causing edges 34 to separate at the slit, creating a flowpath-defining orifice through which liquid may pass in or out of lumen 28 when distal end 14 of catheter 12 is indwelling.

When the indwelling pressure inside lumen 28 exceeds the indwelling pressure outside distal end 14 of catheter 12 by a predetermined amount (the "infusion threshold"), valve 18 immediately surrounding each slit deforms, and edges 34 of wall segments 36 are caused to separate in an outward direction thereby creating an orifice through which liquid is infused into the blood stream, as shown in FIG. 3a. Likewise, the application of a sufficient degree of negative pressure (the "withdrawal threshold") to lumen 28 will cause wall segments to flex hingedly inwardly, as shown in FIG. 4a, allowing withdrawal of blood or other fluids from the bloodstream or other body cavities.

Under normal physiological conditions, as stated above, valves 16 and 18 remain closed and edges 34 remain in an abutted position, as shown in solid lines in FIG. 2a. This requires that catheter 12 have sufficient memory to return to the closed abutted edge-to-edge position when liquid flow conditions terminate. When used in the cardiovascular system, the withdrawal threshold must also be high enough to prevent back bleeding under normal systolic pressures in the circulatory system of a patient. The infusion threshold must likewise be high enough to overcome the normal venturi effect of blood flowing past the indwelling valve. The infusion and withdrawal thresholds should not be so high as to make infusion or withdrawal difficult.

Depending on whether the catheter is a single or a multi-lumen catheter, the flexing of each valve is due to mechanical or chemical treatment of the material from which each valve is made. Treating the material increases the flexibility of the valves formed therein. Although valves in a single lumen catheter may be treated mechanically or chemically, valves in a multi-lumen catheter can only be effectively treated by mechanical means.

In the preferred embodiment of the single lumen version of the present invention, the valves are chemically treated, or softened, by performing several operations on catheter 12 prior to the formation of the valves. Catheter 12 is first cured and distal end 14 is plugged and tipped. Tipped catheter 12 is then suspended from a rack so that the distal (i.e., tipped) end 14 is submerged in an appropriate chemical for catheters made of silastic rubber. Dow Corning 360 Medical Fluid, a polydimethylsiloxane fluid, is an effective chemical-softening agent for that purpose.

Catheter 12 is allowed to soak in the 360 Medical Fluid for times ranging from about 24 hours to about 96 hours. (As an example, a catheter having a wall diameter of about one millimeter would have to be allowed to remain in the 360 medical fluid for about 92 hours to arrive at a 31 Shore A durometer.)

During this soaking process, the 360 Medical Fluid is absorbed into the polymer structure of catheter 12; this softens the measurable durometer of catheter 12 that is in contact with the 360 Medical Fluid to approximately 50% of its original durometer. The 360 Medical Fluid also migrates axial to a small degree through catheter 12, so there is a gradual change in durometer between the portion of catheter 12 that was placed in the 360 Medical Fluid and that portion of the wall of catheter 12 that was not in contact with the 360 Medical Fluid.

After the prescribed soaking time has elapsed, catheter 12 is removed from the 360 Medical Fluid and wiped to remove the excess 360 Medical Fluid from the surface of catheter 12. Catheter 12 is then placed in a fixture, and the valves are cut through the wall of catheter 12. Valves cut through the treated or submerged portion of catheter 12 will have a different durometer than valves cut through the untreated side of catheter 12.

In another embodiment, a larger segment of distal end 14 of catheter 12 is submerged in the 360 Medical Fluid than in the previous embodiment. After soaking for a period of time, a portion of the submerged area of catheter 12 is removed from the 360 Medical Fluid while still leaving the most distal portion of catheter 12 submerged in the 360 Medical Fluid. Finally, all of catheter 12 is removed from the 360 Medical Fluid, as previously discussed.

This embodiment generates a catheter having three different durometer levels. The unsubmerged portion of catheter 12 retains its original durometer level, while the submerged portions of catheter 12 have a measurable durometer change due to the 360 Medical Fluid. Because of the difference in time in which the most distal end portion of catheter 12 and the other submerged portion were in contact with the 360 Medical Fluid, the two submerged portions vary in their durometer levels. The most distal end of catheter 12 experiences the greatest change in durometer level because it was submerged in the 360 Medical Fluid for the longest period of time.

Alternatively, after catheter 12 is cured and distal end 14 is plugged and tipped, catheter 12 can be suspended from a rack along its side so that one-half of catheter 12 along its longitudinal axis is submerged in the 360 fluid. That half of catheter 12 submerged along its side to the 360 Medical Fluid experiences a change in its durometer level. Catheter 12 is similarly allowed to remain in the 360 Medical Fluid for times ranging from about 24 hours to about 96 hours.

In the preferred embodiment of the chemical treatment of catheter 12, catheter 12 is manufactured with silicone tubing that has been extruded from two-part silicone elastomers that have different durometers. These extruded tubes currently are received in two durometer ranges: Shore A durometer of 45 to 55, and Shore A durometer of 60 to 70. These are preferable because they have an already low durometer level and do not require to a great extent further changes in durometer levels by mechanical or chemical treatments. The extruded tubing is received and subjected to several processing steps that modify the durometer of the tubing used to manufacture catheter 12 or that modify the durometer of a specific section of catheter 12.

Catheter 12 (which is a typical intravascular long term indwelling catheter may be 100 cm long) has about 1.5 to about 2.5 centimeters of distal end 14 soaked in Dow Corning 360 Medical Fluid for the specific purpose of softening the durometer of this portion of catheter 12. The soaking time has been determined experimentally to make sure the durometer becomes soft enough to ensure the proper valve function. The amount of time that catheter 12 must soak is dependent upon the original durometer range of the tubing. The soaking time is controlled to yield varying durometer ranges for distal end 14 of catheter 12.

Application of the 360 Medical Fluid decreases the durometer of wall segments 36. The durometer of wall segments 36 after treatment can expect to have a durometer from about 10 to about 45 Shore A. In one embodiment of the present invention, valves have a Shore A durometer in the range from about 20 to about 35 Shore A. In the preferred embodiment, however, valves have a Shore A durometer in the range from about 24 to about 31 Shore A.

Catheters having wall segments 36 with a durometer higher than about 70 Shore A are unable to operate consistently. In other words, at a given pressure differential, wall segments 36 will not open or close reproducibly. More often than not, it is the case where wall segments 36 remain closed at a pressure differential for which they had previously opened. This detrimental result is emphasized during operation of a catheter during low pressure differentials.

Operating a catheter when applying low pressure differentials is less demanding upon the catheter than operating a catheter when applying high pressure differentials. Although the application of a high pressure differential at proximal end 20 of catheter 12 would unlikely result in blow-out or rupture of catheter 12, certain environments are not receptive to high pressure differentials by a catheter for infusion or aspiration of a fluid. An example of such an environment is the body tissues of a patient undergoing chemotherapy treatment where the rapid administration of chemical fluids to a specific body tissue can cause necrosis or damage to the body tissues or to the patient himself.

The application of a low pressure differential at proximal end 20 of catheter 12, on the other hand, allows catheter 12 to be employed in many environments. Fluids need not be moved at a high velocity due to pressure differentials; sometimes the rapid withdrawal of fluids can be dangerous to a patient, causing trauma to tissues.

It should also be noted that the valve may, if desired, be treated with an anticoagulant, such as Heparin, or a cooling that minimizes cellular adhesion and growth. However, the design of the catheter disclosed herein does not require such treatment in order to be successfully manufactured.

In another embodiment of the present invention, the valves are mechanically treated, or weakened, by placing a slit in wall layer 32 of catheter 12. The degree to which the valves are weakened is controlled by the sizes and shapes of the slits forming the valves. As discussed below, the sizes and shapes may be varied in many ways.

In one way, lumen 28 may be placed in an off-center, or in eccentric relation to exterior surface 30 of catheter 12. The thickness of wall layer 32 about lumen 28 varies according to the eccentric placement of the lumen in relation to exterior surface 30 of catheter 12 because of the D-shape of the lumen. According to the thickness of wall layer 32 of catheter 12, the mechanical weakness of a slit formed therein may be varied.

As seen in FIGS. 2a, 3a, and 4a, lumen 28 of catheter 12 is placed in eccentric relation to the exterior surface of catheter 12. The thickness of wall layer 32 at distal slit valve 18 is less than the thickness of wall layer 32 at proximal slit valve 16. Because the wall thickness between lumen 28 and the exterior of catheter 12 at proximal valve 16 is greater than the wall thickness at distal valve 18, edges 34 at proximal valve 16 are less flexible and require a greater amount of threshold pressure to flex into an open arrangement than do edges 34 of distal valve 18. Thus, in another manner of speaking, by mechanically decreasing the wall thickness between lumen 28 and the exterior of catheter 12, distal valve 18 can be made weaker, and flex into an open position as illustrated in FIGS. 3a and 4a at a lower pressure differential threshold than proximal valve 16.

Another way to mechanically control the degree of the threshold pressure necessary to move valves into an open position is to vary the valve lengths; in other words, the slit in wall hinge 38 of catheter 12 may be of different lengths. Valves with longer slits have more flexible edges which require a lower amount of a threshold pressure differential to flex the edges of the valve in an open arrangement. Experimentation has indicated valve lengths of about 0.150 to about 0.450 inches operate effectively.

A more comprehensive discussion of the valve lengths can be made by reference to FIG. 1. The distal valve 18 of FIG. 1 is mechanically weaker than proximal valve 16 due to the fact that distal valve 18 has a slit length in the range from about 0.340 to about 0.360 inches, whereas proximal valve 16 has a slit length in the range from about 0.190 to about 0.210 inches. The present invention is not limited to the foregoing valve lengths, however. Distal valve 18 may be in the range from about 0.330 to about 0.370 inches while proximal valve 16 is in the range from about 0.180 to about 0.220. Still further, distal valve 18 may be in the range from about 0.300 to about 0.400 inches while proximal valve 20 is in the range from about 0.150 to about 0.250 inches.

As depicted in FIG. 1, the degree of the threshold pressure necessary to move distal valve 18 and proximal valve 16 into an open position has been mechanically controlled by varying the length of the slits made to form distal valve 18 and proximal valve 16. Distal valve 18 has a longer slit than proximal valve 16. Thus, edges 34 of distal valve 18 are more flexible than edges 34 of proximal valve 18 and therefore, a lower amount of a threshold pressure differential is necessary to flex edges 34 of distal valve 18 in an open arrangement than edges 34 of proximal valve 16.

The predetermined liquid pressure differentials pivot edges 34 into a spaced-apart spatial relationship, whereby edges 34 are capable of opening either outwardly or inwardly. As seen in FIG. 3a, when edges 34 flex outwardly from the normally abutted and closed position, the fluid is infused from the one of the lumens into the space exterior to distal end 14 of catheter 12. When the edges flex inwardly from the normally abutted and closed position, the fluid is withdrawn from the space exterior to distal end 14 of catheter 12 into the one of the lumen 28 in the path represented by Arrow B. Those edges which are mechanically treated are capable of opening at a lower threshold pressure differential than those edges which are untreated (in FIGS. 3a and 4a, proximal valve 16 remains closed while distal valve 18 remains open).

A plurality of three-position valves are placed in the wall layer 32 adjacent to and laterally interfacing with at least one lumen adjacent distal end 14 of catheter 12. In the preferred embodiment of the present invention illustrated in FIG. 1, only two three-position valves 16 and 18 are placed adjacent to and laterally interfacing with one lumen adjacent distal end 14 of catheter 12. Where a plurality of lumens are employed in catheter 12, one may choose to employ the plurality of three-position valves in one, more than one, or all of the lumens available. As seen in FIG. 1, valves 16 and 18 are formed by a single relatively short slit in wall layer 32. Each slit extends longitudinally along the exterior of distal end 14 of catheter 12. The thickness of each slit valve is equal to the thickness of wall layer 32, so as to provide for liquid communication between the interior of lumen 28 with the exterior of distal end 14 of catheter 12. Each slit valve is illustrated as being radially directed and symmetrically disposed in lumen 28 at the thinnest point in wall layer 32. Thus, each slit valve comprises two wall segments 36 which comprise blunt edges 34. Edges contiguously mate and abut along the slit under normal indwelling pressure conditions.

It is important to note that the present invention does not only provide for a plurality of valves in catheter 12, but also that the valves have individual operational properties. In the preferred embodiment of the present invention, illustrated in FIG. 1, valve 18 (sometimes referred to as the primary or distal valve) located distal from valve 16, opens at a lower threshold pressure differential than valve 16 (referred to as the secondary or surrogate valve). Thus, as illustrated in FIGS. 3 and 4, at a pressure differential sufficient to place valve 18 in an open position, but insufficient to place valve 16 in an open position, valve 18 will be preferably operating to the exclusion of all other valves in catheter 12 (or, if multi-lumen, all other valves in that lumen).

Of course, if increased pressure differentials are employed, higher than the threshold pressure level of both valves 16 and 18, both valve 16 and 18 will be placed in an open position. This is important because, should the preferably operating valve (e.g., valve 18) become unable to operate, another valve (e.g., valve 16) can remain open even though the preferably operating valve is not capable of having fluids aspirated or infused therethrough. The valve not capable of having fluids aspirated or infused therethrough may be blocked because of the suction of the catheter against a solid surface or a coagulated mass. Alternatively, the valve not capable of having fluids aspirated or infused therethrough may be wedged against a vessel wall due to the narrowness of the vessel at that point.

Most open-ended catheters experience difficulty or inability to withdraw fluids through the catheter while retaining the ability to infuse fluids. This result occurs because the opening in the catheter, whether it be a valve or open tip, can readily become partially or totally occluded during aspiration by the exterior surroundings of catheter 12. Infusion may still be allowed because infused fluids would constantly push materials away from the occluded valve.

Figure 5:
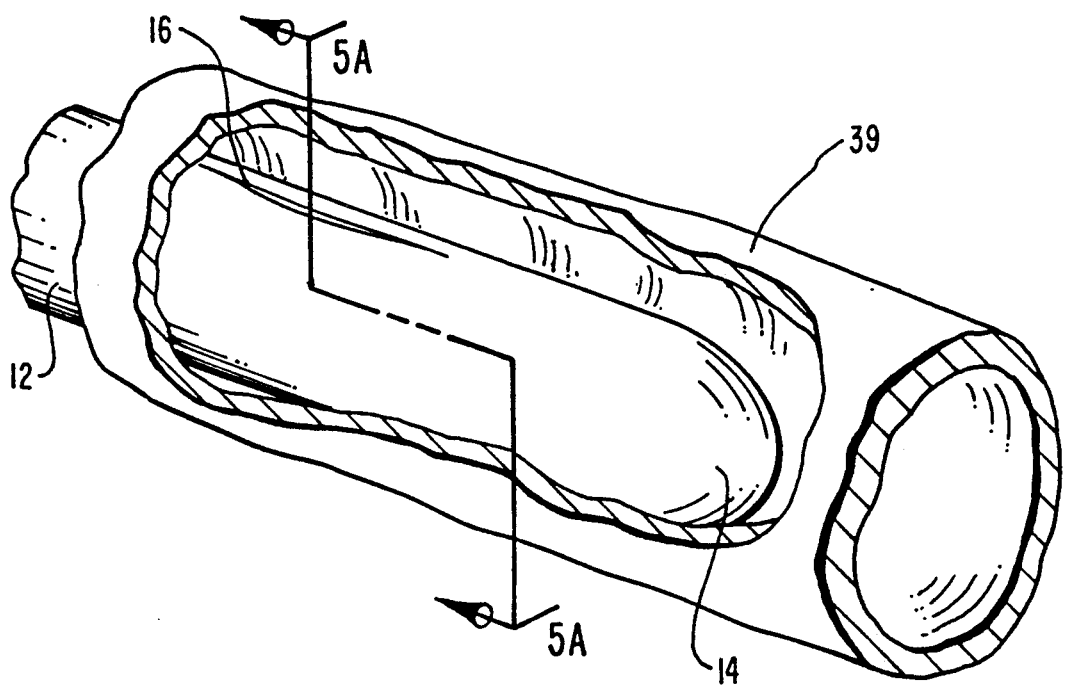
FIG. 5 is a perspective view of the present invention wherein the distal valve is totally occluded by an adjacent vein and the proximal valve acts as a surrogate to the distal valve to aspirate fluids.
Figure 5A:
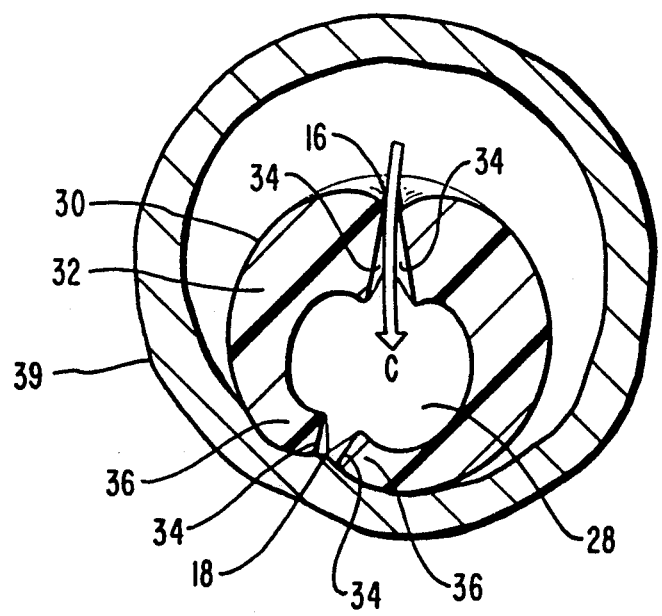
FIG. 5a is a cross-sectional view of the catheter taken along line 5a of FIG. 5 in which the proximal valve is in an open inwardly flexed position, acting as a surrogate to the occluded distal valve to aspirate fluids.

The present invention places a second valve on the side of catheter 12 to act as a surrogate to a blocked first valve, as shown in FIGS. 5 and 5a. In FIG. 5, the primary or distal valve 18 (not shown in FIG. 5, but shown in FIG. 5a) becomes inoperable for aspiration because it is wedged against vein 39. The presence of proximal valve 16 allows catheter 12 to continue aspiration in spite of blocked distal valve 18.

Proximal valve 16 opens after the negative pressure differential threshold for proximal valve 16 is achieved. Unless the fit of catheter 12 in vein 39 is quite tight to block proximal valve 16, proximal valve 16 continues to permit aspiration in the normal manner. Thus, proximal valve 16 acts as a back-up or surrogate to blocked distal valve 18 to allow aspiration to continue.

The position of the valves when distal valve 18 is blocked can be further illustrated in FIG. 5a, wherein a cross-sectional view is taken along line 5a of FIG. 5. As depicted, edges 34 of distal valve 18 are flexed inwardly in response to the negative pressure differential applied to lumen 28 of catheter 12. Nevertheless, because vein 39 blocks the open space between edges 34, aspiration therethrough distal valve 18 is prevented.

As a result of blocked distal valve 18, proximal valve 16 responds to a sufficient threshold pressure differential. As depicted, edges 34 of proximal valve 16 are flexed inwardly in response to the negative pressure differential applied to lumen 28 of catheter 12. Thus, the negative pressure differential is sufficient not only to open distal valve 18 preferably, but opens proximal valve 16 as well to allow aspiration of fluids which is prevented through distal valve 18. The path taken by the aspirated fluids through proximal valve 16 is shown by Arrow C.

The individual operational properties of catheter 12 is important not only during aspiration, but during infusion where it is preferred that the most distal valve operates preferably before any other valves. Generally, when a catheter is constructed for infusion, a valve is placed at the most distal end of a catheter to ensure that all of the infused liquid is removed from the lumen of the catheter. Valves placed proximal to the end of a catheter leave what is known as "dead space," or a reservoir, at the end of the catheter lumen.

The dead space at the end of the catheter lumen has no means for the removal of liquid that collects therein. This reservoir is an active site for contamination or the clotting of blood. The contaminants can commingle with fluids transmitted thereafter through a catheter lumen, and lead to infection in a patient. Thus, valves need to be placed near the distal end of a catheter to minimize any dead space, and possible infection caused thereby.

A problem exists, where a plurality of valves are desired for the reasons previously discussed. It is possible that more than one valve may be placed at the distal end of a catheter, but one risks the loss of structural integrity at a catheter tip. Thus, as it will be discussed at a later point in greater depth, the valves of the present invention are spaced longitudinally from one another. This presents a problem, however, because if proximal valve 16 operates before distal valve 18, dead space occurs from which infection can arise.

It is in this light that a novel feature of the present invention is provided. By forming valves which have individual operational properties, distal valve 18 is designed to open first to prevent the accumulation of a reservoir at distal end 14 of catheter 12. Proximal valve 16 acts as a surrogate to distal valve 18 without a significant pressure change should distal valve 18 fail to operate, such as during aspiration if distal end 14 becomes partially or totally occluded.

The ways in which the individual operational properties of the valves are determined have been discussed previously. By differentiating the amount of mechanical or chemical treatment between the valves, a difference occurs in the lowest threshold pressure differential upon which the valve will flex in an open position. Thus, if distal valve 18 is treated to a greater degree than proximal valve 16, distal valve 18 will have a lower threshold pressure differential than proximal valve 16, and open at that pressure differential to the exclusion of proximal valve 16.

Nevertheless, as discussed, proximal valve 16 can act as a surrogate to open should distal valve 18 become partially or totally occluded. Moreover, by decreasing the difference between the threshold pressure differentials between distal valve 18 and proximal valve 16, proximal valve 16 can open without a significant change in the pressure differential applied to the fluid in the lumen.

Before differentiating the amount of mechanical or chemical treatment between the valves, the threshold pressure differential employed for any valve must be determined. The primary valve, or first valve to open, being set at a lower threshold pressure differential than the secondary valves acts as a surrogate to the primary valve. Valves set to open at pressure differentials that are too high will not open consistently and reproducibly. Likewise, valves set to open at pressure differentials that are too low will tend to open prematurely, leading to dead space.

The combination of the catheter and valve is designed to allow injection and aspiration at the user's discretion. The valve resists opening prematurely, however, when subjected to forces that the body may impart on the catheter because of the catheter's position in the vascular system. In order for the valve to support a fluid column within a catheter that has a single valve (regardless of catheter size), it must withstand certain pressure ranges.

It is at certain pressure differential ranges that a valve reproducibly and consistently moves into an inwardly or outwardly open position, thus allowing for the aspiration or infusion of fluids between the exterior and the lumen of a catheter. Valves that operate reproducibly and consistently are more reliable to individuals that depend upon aspiration under certain conditions. These individuals need not worry about the valve being stuck in a closed position or opening prematurely.

"Push Pressure" is defined as the pressure that the valve must resist when the patient's blood pressure is compressing the catheter, i.e., the pressure required to push the valve into the lumen of the catheter and to allow the blood to enter the lumen. For single-valved catheters, a pressure differential in the range from about 1.5 psig to about 10.0 psig is employed. In other single-valved catheters, a pressure differential in the range from about 2.0 psig to about 9.0 psig may be employed.

Preferably in single-valved catheters, a pressure differential in the range from about 4.0 psig to about 7.0 psig is employed.

"Pull Pressure" is defined as the pressure that the valve must resist when the flow of the patient's blood past the valve pulls the valve out of the lumen allowing fluid to be pulled into the blood stream, i.e., the venturi affect. In single-valved catheters, a pressure differential in the range from about 0.3 psig to about 2.0 psig is employed. In other single-valved catheters, a pressure differential in the range from about 0.6 psig to about 2.0 psig may be employed.

Preferably, in single-valved catheters, a pressure differential in the range from about 1.0 psig to about 2.0 psig is employed.

In catheters with multiple valves per lumen (regardless of catheter size), the valves must withstand certain pressure ranges in order to support a fluid column in the catheter. With regard to push pressure, in one embodiment of the present invention, a pressure differential in the range from about 1.5 psig to about 10.0 psig is employed. In another embodiment, a pressure differential in the range from about 2.0 psig to about 9.0 psig is employed. Preferably, a pressure differential in the range from about 3.0 psig to about 6.0 psig is employed.

With regard to pull pressures, in one embodiment of the present invention, a pressure differential in the range from about 0.3 psig to about 2.0 psig is employed. In another embodiment, a pressure differential from about 0.5 psig to about 2.0 psig is employed. Preferably, a pressure differential in the range from about 0.9 psig to about 1.7 psig is employed.

Some concern exists that the placement of two valves at the same longitudinal position on a catheter, albeit opposite sides thereof, could unduly weaken the catheter tip. Accordingly, in the preferred embodiment of the present invention, valves 16 and 18 are radially displaced from each other (preferably by about 10° to about 180° in single lumen catheters in order to maximize distance while minimizing the effect of reducing structural strength) while still ensuring structural integrity near distal end 14 of catheter 12. The valve sites of the present invention are radially distributed in offset relation around distal end 14 of catheter 12 near the tip so that no two valves lie in any one radial plane. While not specifically pictured, valve sites may be radially distributed in offset relation around each of the lumens included in a multi-lumen catheter, although the radial distribution is limited due to the nature of multi-lumen catheters.

The present invention also displaces the second slit valve longitudinally from the first slit valve by an appropriate distance. The valves are longitudinally separated or offset in their placement at relatively short but different distances from distal end 14 of catheter 12 so that no two valves lie in any one axial plane.

The radial and longitudinal separation of the valves helps avoid structural weakness and helps prevent possible contamination of an influent sample withdrawn from one valve by an infusion stream of effluent liquid from another valve passing into the vein of a patient, which might adversely affect test results or results in premature mixing of incompatible therapeutic liquids. It should be noted that longitudinal separation should not be used where the effect would be to position any valve out of the desired treatment or exposure area.

In FIG. 1, valves 16 and 18 are longitudinally displaced from each other while still providing structural integrity at distal end 14 of catheter 12. In the preferred embodiment of the present invention, valves 16 and 18 are longitudinally staggered from each other so that the distal end of proximal valve 16 is at level of the proximal end of distal valve 18.

Figure 6:
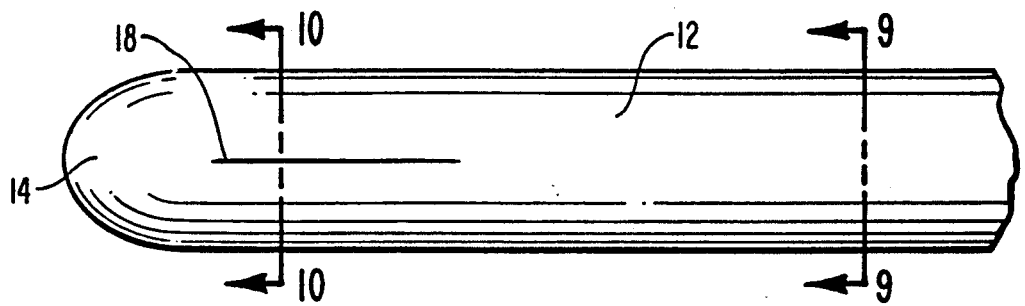
FIG. 6 is a left-side view of the catheter showing therein a first valve.
Figure 7:
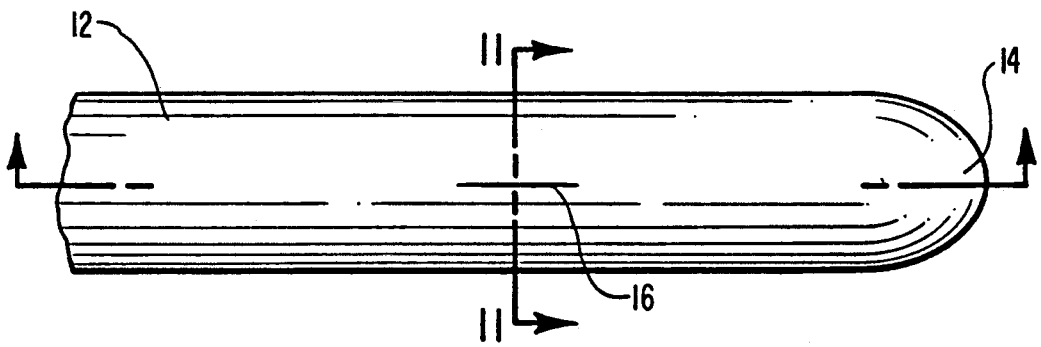
FIG. 7 is a right-side view of the catheter showing therein a second valve.
Figure 8:
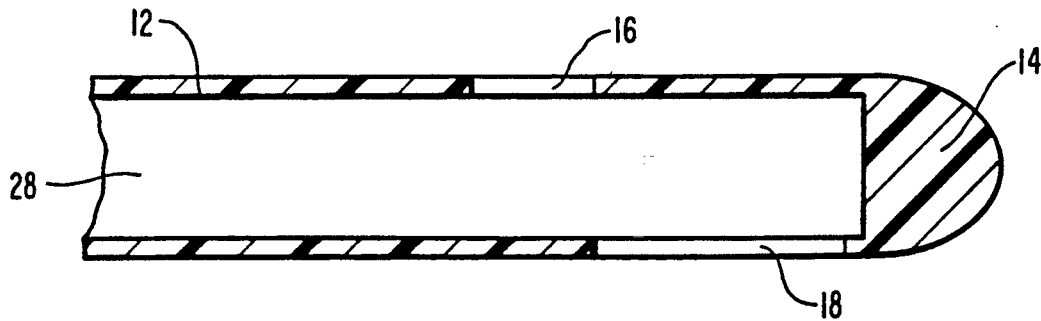
FIG. 8 is a longitudinal cross-section of the catheter taken along line 8—8 of FIG. 7.

The longitudinal displacement can be understood by referring to FIG. 6 wherein distal valve 18 is formed on the left side of catheter 12 In FIG. 7 proximal valve 16 is formed on the right side of catheter 12. FIG. 8 is a longitudinal section taken along line 8—8 of FIG. 7 illustrating the space vertically and horizontally between valves 16 and 18 due to valves 16 and 18 having radial and longitudinal displacement from each other.

FIG. 8 not only illustrates how valves 16 and 18 are spaced longitudinally and radially to ensure structural integrity at distal end 14 of catheter 12, but also illustrates the mechanical weakening of distal valve 18 in relation to proximal valve 16. The length of the slit made to form proximal valve 16. Thus, because of the mechanical weakening of distal valve 18 in relation to proximal valve 16, edges 34 of distal valve 18 are capable of moving into an open position in response to the application of a pressure differential before edges 34 of proximal valve 16.

Figure 9:
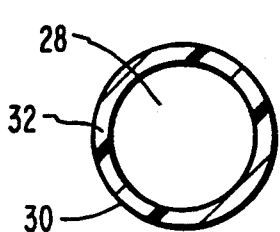
FIG. 9 is a cross-sectional view of the catheter taken along line 9—9 of FIG. 6.
Figure 10:
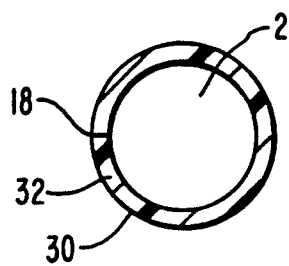
FIG. 10 is a cross-sectional view of the catheter taken along line 10—10 of FIG. 6.
Figure 11:
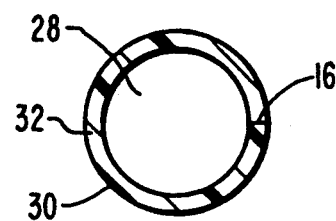
FIG. 11 is a cross-sectional view of the catheter taken along line 11—11 of FIG. 7.

FIGS. 9-11 are cross-sectional views taken along lines 9—9, 10—10, and 11—11 of FIGS. 6 and 7, illustrating the space vertically and horizontally between valves 16 and 18. No valves are present in FIG. 9. Distal valve 18 is represented at the left side of catheter 12 in FIG. 10. Proximal valve 16 is represented at the right side of catheter 12 in FIG. 11.

Figure 15:
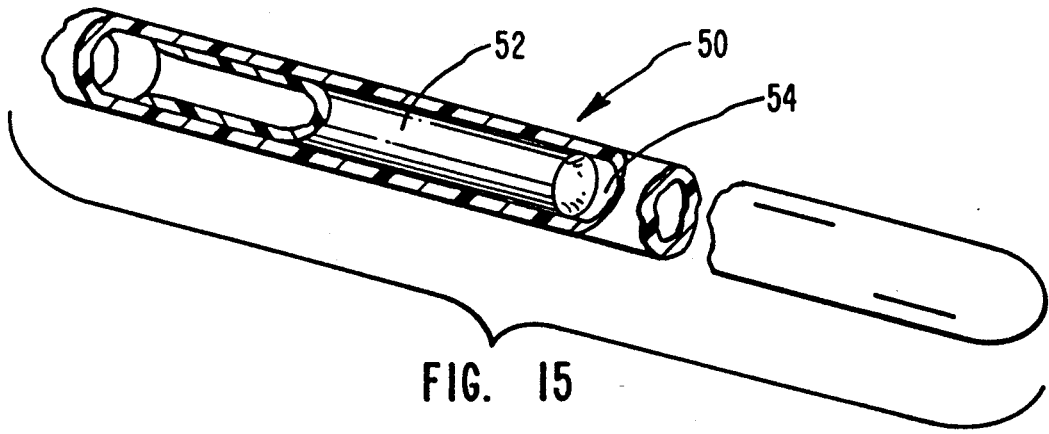
FIG. 15 is a perspective view of an alternate embodiment within the scope of the present invention illustrating a reinforcing means within the lumen of the cannula.

In another embodiment of the present invention, illustrated in FIG. 15 it is proposed that where a catheter 50 has a region subject to compressive forces while it is placed in a patient, to provide reinforcing means. The reinforcing means would be positioned within a lumen 54 of the catheter for site-selectively reinforcing the aforesaid region of the catheter where the compressive forces are applied against catheter 50. The compressive forces could be generated anywhere along catheter 50. The reinforcing means as illustrated in FIG. 15 are preferably nonmetallic inner tubular sleeves 52 capable of withstanding compressive forces generated by the body or a patient. The inner tubular sleeve 52 is inserted site-selectively within the cannula. The methods and apparatus for reinforcing catheter 50 can be more clearly understood by reference to U.S. patent application Ser. No. 07/665,787, filed Mar. 7, 1991, in the name of H. Robert Moorehead, which is incorporated into this application by specific reference.

Figure 14:
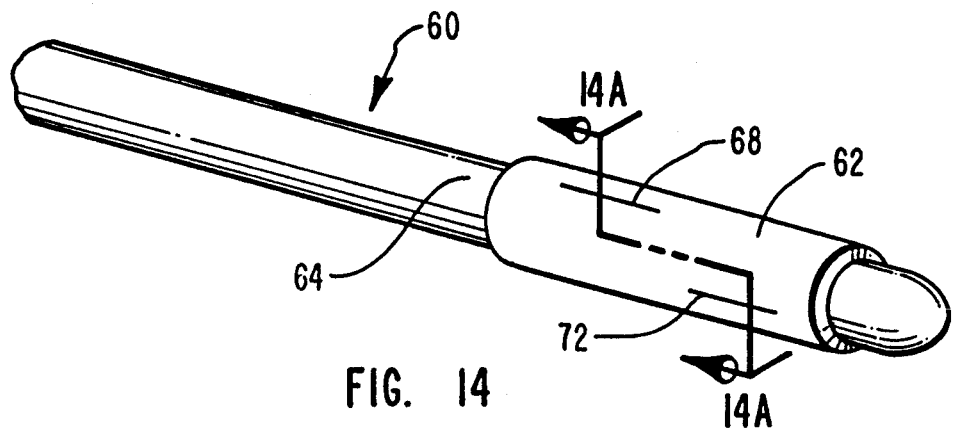
FIG. 14 is a perspective view of an alternate embodiment within the scope of the present invention illustrating a length of tubing enclosing the valves.
Figure 14A:
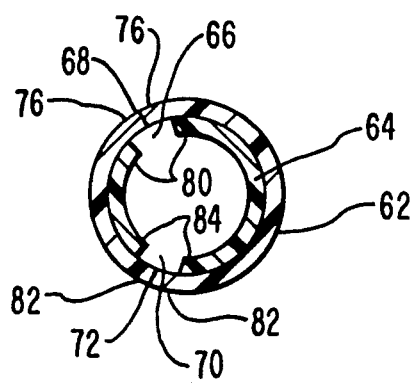
FIG. 14A is a cross-sectional view of the catheter taken along line 14A of FIG. 14.

In still another embodiment of the present invention, as illustrated in FIGS. 14 and 14a valves of catheter 60 are formed without the provision of a simple slit. Catheter 12 includes a length of tubing 62 mounted to a cannula tube 64 and extending along a relatively short distal end segment thereof. This embodiment includes include means defining a first aperture 66 in the tube wall of cannular tube 64 directly opposite and surrounding a primary valve 68, and a second aperture 70 in the wall of cannula tube 64 directly opposite a secondary valve 72. Each aperture 66 and 70 is wider than its corresponding valve so that first tubing wall portions 76 on opposite sides of the primary valve 68 overhang the first opposite edges 80 of first aperture 66 and second tubing wall portions 82 on opposite sides of the secondary valve 72 overhang the second opposite edges 84 of second aperture 70.

This embodiment enables the valves of the present invention to have characteristics independent of the material of which the catheter is made. Therefore, the catheter may be made from relatively stiff material to facilitate its insertion into a patient and/or its connection to an implanted vascular access port without materially affecting the operation of the valves at the distal end of the catheter.

Figure 12:
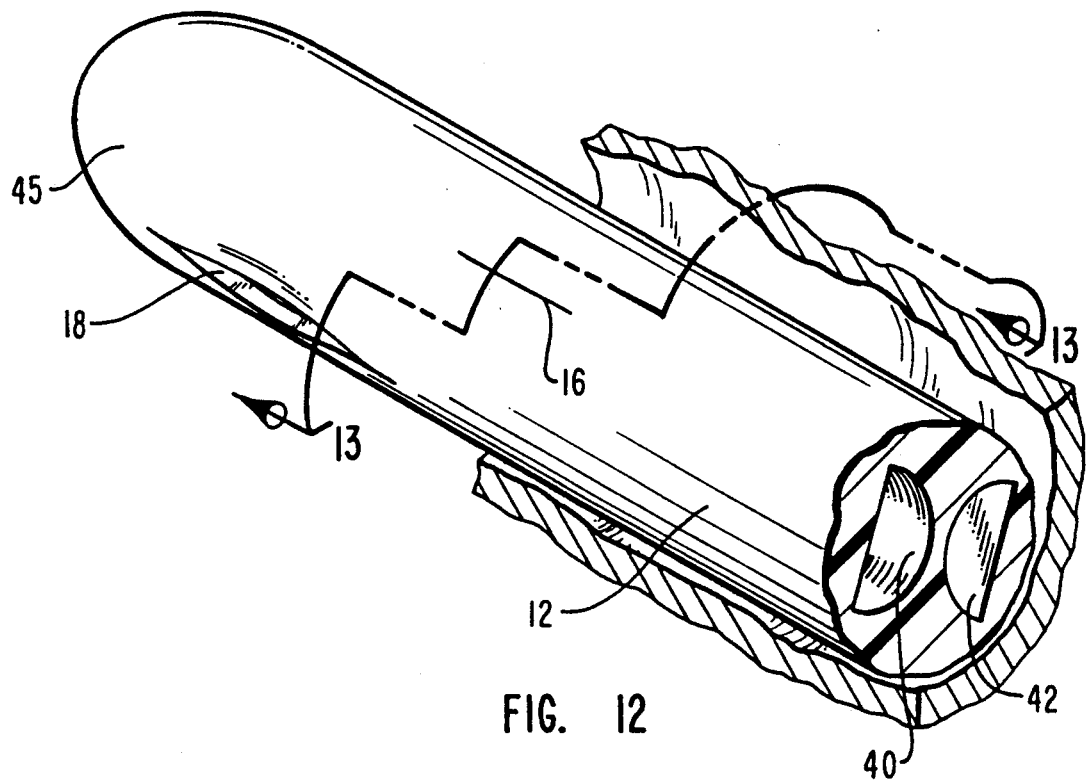
FIG. 12 is a perspective view of another embodiment of the present invention comprising a multi-lumen catheter.

As discussed previously, catheter 12 may include more than one lumen. As illustrated in FIG. 12, two independent lumens 40 and 42 are longitudinally disposed inside wall layer 32 of catheter 12. Lumens 40 and 42 typically are radially distributed at predetermined angles beneath the exterior cylindrical surface of catheter 12 in such a way that an interior lumen wall surface passes within a relatively short distance of the exterior surface of the exterior wall layer 32, as measured along a radial line passing through the center of each lumen.

It is apparent from the radial disposition of lumens 40 and 42, in close proximity to the exterior surface valves 46-49 (valves 48 and 49 not shown in FIG. 12, but shown in cross-section in FIG. 13) installed along a radial line in the fashion just described or installed in any consistent position relative to lumens 40 and 42, will necessarily be radially separated from each other as previously discussed. Interior walls respectively form and define the size and shape of lumens 40 and 42. Tubular, hollow walls respectively form and define the size and shape of lumens at the proximal end portion.

Each lumen extends from the associated hub at proximal end 20 of catheter 12 to a point near the distal tip 45. The larger or primary lumen 40 extends substantially the entire length of catheter 12, terminating in a closed tip wall portion adjacent distal tip 45. The secondary lumen 42 terminates in similar closed end wall portions. Lumen 40 and 42 terminate at relatively short, but different, distances from distal tip 45 for the purpose of providing longitudinal separation of valves 46-49, as previously discussed.

In the embodiment of FIG. 12, proximal end 20 is preferably formed by extrusion, for reasons of simplicity and ease of construction, but other methods may be used. When extruded, lumens 40 and 42 and the interior walls forming lumens 40 and 42 are continuously formed during extrusion; thus, each lumen is of a uniform cross-sectional shape, nevertheless lumens 40 and 42 may be D-shaped as in the embodiment of FIG. 12.

In catheter 12, closed end wall portions are formed by injecting a suitable silicone rubber adhesive or the like into the leading ends of lumens 40 and 42 and for the distance from distal tip 45. The adhesive then hardens to form the closed end wall portions, each up to the leading edge of the associated valve. If a radiopaque distal tip is desired, this may be accomplished by mixing a radiopaque material with the adhesive prior to injection to form the closed end wall portions.

The liquid flow capacity of lumens 40 and 42 may vary with the intended application of catheter 12. Lumens 40 and 42 must, of course, be large enough to accommodate the desired fluid flow, while the thickness of the walls forming the lumens, when more than one lumen is employed, must be adequate to prevent rupture or inadvertent puncture and consequent leakage either between lumens or to or from the exterior.

Valves 46-49 must be located at the weakest point in each lumen 40 and 42. Each part of wall layer 38 about each catheter lumen must be stronger and more rigid than the wall segments 36 comprising valves 46-49; otherwise the catheter would collapse, defeating the purpose of catheter 12. It is, therefore, important that the lumen walls be strong enough to stand the full range of lumen pressures without inward collapse or other failure, which would impair proper operation of valves 46-49.

Each tube may, therefore, be strengthened by using a tubing with thicker walls and/or a higher durometer. Tubes are preferably at least partially transparent or translucent to accommodate visual monitoring of the contents therein at the proximal end of the catheter. Unlike distal end 14', however, the proximal tubes have no need for radiopacity, because they are not intended to be indwelling.

Figure 13:
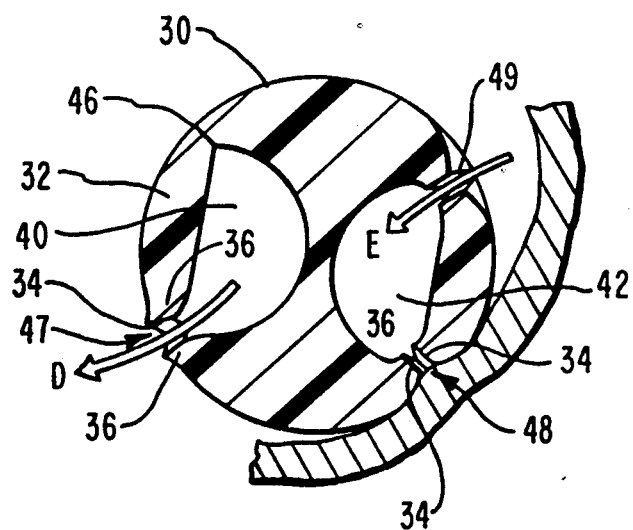
FIG. 13 is a cross-sectional view of the valves of the multi-lumen catheter taken along line 13—13 of FIG. 12.

A greater understanding of the operation of catheter 12 with dual lumens 40 and 42 can be made by reference to FIG. 13 wherein valves 46-49 are illustrated. In this figure, catheter 12 is performing aspiration and infusion of fluids between lumens 40 and 42 and the exterior of distal tip 45 of catheter 12. Infusion is performed through valve 47 of lumen 40; aspiration is performed through valve 49 of lumen 42.

The teachings of the present invention are present in the multi-lumen catheter illustrated by FIGS. 12 and 13. Valve 47 is preferably operable to valve 46 to infuse fluids in the path set forth by Arrow D from lumen 40 to the exterior of distal tip 45 of catheter 12. As shown in FIG. 12, preferable operation of valve 47 is a result of the greater length of the slit forming valve 47 than the length of the slit-forming valve 46. Thus, the preferable operation of valve 47, located distal to valve 46, minimizes the remains of infused fluids at distal tip 45 since valve 47 opens preferably to valve 46 at certain pressure differentials. Valve 49 is preferably operable to valve 48 to aspirate fluids in the path set forth by Arrow E from the exterior of distal tip 45 of catheter 12 to lumen 40. Although not shown, preferable operation of valve 49 is a result of the greater length of the slit forming valve 49 than the length of the slit-forming valve 48. Thus, the preferable operation of valve 49, located distal to valve 46 acts as a surrogate to allow aspiration of fluids, such as blood, in spite of the fact that valve 48 is wedged against a vein.

It will be recognized that a central feature of the invention is that the infusion and withdrawal thresholds of each valve may be selected to meet the needs of any particular application. It is also to be noted that while the mechanically weakened valve is of particular importance in multi-lumen catheters, the principles thereof, comprising part of the present invention, still apply to single-lumen catheters.

EXAMPLES

Example 1

Several catheters were evaluated to determine the minimum threshold-opening pressure for infusion and the minimum threshold opening vacuum for fluid removal. Seven catheter groups (with five catheters in each group) of differing material of construction and valve configuration were evaluated.

The experimental design consisted of testing catheters made from silicone rubber ("SR"), and silicone rubber treated with 360 Medical Fluid ("SRw/S"). The SR catheters were also evaluated using both two and six valves per catheter. The SRw/S catheter was only evaluated with two valves. The catheters were evaluated with an automated test apparatus. The test apparatus was checked for calibration to the National Bureau of Standards and Technology ("NIST").

The test apparatus consisted of the sensitive pressure transducer and associated fittings and connectors. The pressure (and vacuum) transducer utilized a programmable digital reading. The transducer was standardized against NIST traceable pressure/vacuum gauge prior to initiation of any test.

Pressure was determined by slowly and consistently increasing the pressure over a small reservoir of water attached to the test catheter. The pressure (which was necessary to open the valve) was automatically recorded by the pressure transducer test apparatus.

Vacuum was determined by placing the test catheters into a small reservoir of water and gradually but consistently increasing the vacuum until flow was established through the catheter. The opening vacuum was stored by the pressure transducer and was recorded for each catheter type and test unit. Vacuum and pressure were checked after each series of five catheters using a NIST traceable gauge.

Minimum valve opening pressures are outlined in Table 1 below.

TABLE 1

| SR catheter w/2 slit valves | 11.7 psig |
|---|---|
| SR catheter w/6 slit valves | 7.4 psig |
| SRw/S catheters w/2 slit valves | 0.4 psig |

Minimum valve opening vacuum levels are outlined in Table 2 below.

TABLE 2

| SR catheter w/2 slit valves | (−)9.7 psig |
|---|---|
| SR catheter w/6 slit valves | (−)11.0 psig |
| SRw/S catheters w/2 slit valves | (−)2.2 psig |

The results indicate that the SRw/S catheters were different from all of the other test groups using vacuum aspiration. ARw/S catheter valves open consistently and at low operating vacuum levels. The other test groups either opened at higher levels or were inconsistent in opening vacuum levels.

The results further showed that the SRw/S catheters also opened consistently and at low operating levels using pressure and infusion. The SRw/6 slit valve catheters opened at intermediate pressures, but not consistently. The SRw/2 slit valve catheters required high operating pressure to open consistently.

The SRw/S catheters were the only test group that performed consistently and at low operating value. All of the SRw/S catheters opened and closed. Thus, the chemical treatment of the SRw/S catheters with silicon oil softens the catheters so that valves formed therein will open at a lower pressure differential threshold than will valves formed in the SR catheters. A primary valve made in an area treated with silicon oil will open at a lower pressure differential threshold than a secondary valve made in an area not treated with silicon oil.

Example 2

Catheters are employed that are similar to the catheters of Example 1, except that the catheters are multi-lumened catheters. The catheters provide for infusion and aspiration of fluids through valves in each of the lumens without complications from tissue blockage.

This example indicates that multi-lumen catheters may provide for a plurality of valves in each lumen with the valves having individual operational properties designed to have a primary valve operating at a lower threshold pressure differential than secondary or surrogate valves which act when the primary valve fails to operate.

Example 3

Catheters are employed that are similar to the catheters of Example 1, except that the catheters are reinforced by a nonmetallic inner sleeve site selectively placed within the catheter lumens (reference to these types of catheters may be made to pending U.S. patent application Ser. No. 07/665,787).

This example indicates that reinforced catheters may provide a plurality of valves in each lumen, the valves having individual operational properties designed to have a primary valve operating at a lower threshold pressure differential than secondary or surrogate valves which act when the primary valve fails to operate.

Example 4

Catheters are employed that are similar to the catheters of Example 1, except that the catheters are intravascular. This example indicates that different types of catheters may be employed providing a plurality of valves in each lumen, the valves having individual operational properties designed to have a primary valve operating at a lower threshold pressure differential than secondary or surrogate valves which act when the primary valve fails to operate.

COMPARATIVE TESTING

Comparative testing was conducted to evaluate the performance of some of the different materials and designs of construction of the present invention as compared to those described in the Cami valve catheter (U.S. Pat. No. 3,885,561 issued on May 27, 1975 to Charles N. Maxel Cami). Comparative testing was conducted to illustrate that the structure of the Cami valve catheter will not function the same as the catheters of the present invention. Results of the Cami valve are reported herewith.

The test was conducted by Nelson Laboratories, Inc. in accordance with the Federal Good Laboratory Practices (21 CFR Part 58). Nelson Laboratories' Quality Assurance reviewed the results and determined that the methods and standard operating procedures were accurately conducted, and that the reported results accurately reflected the raw data. The test apparatus was checked for calibration to NIST standards.

The test apparatus consisted of the sensitive pressure transducer and associated fittings and connectors. The threshold opening pressure and vacuum values were determined according to the procedures outlined in Example 1.

The experimental design consisted of testing catheters made from polyvinylchloride ("PVC"), as well as those types of catheters tested in Example 1, such as SR and SRw/S. The Cami patent discloses that its catheters are made of PVC, and therefore the following tests conducted with PVC equate with tests conducted on the disclosures of Cami. The SR and PVC catheters were evaluated using both two and six valves per catheter. The SRw/S catheter was only evaluated with two valves.

Minimum valve opening pressures test are outlined in Table 3 below.

TABLE 3

| PVC catheter w/2 slit valves | 13.8 psig |
| --- | --- |
| PVC catheter w/6 slit valves | 1.2 psig |
| SR catheter w/2 slit valves | 11.7 psig |
| SR catheter w/6 slit valves | 7.4 psig |
| SRw/S catheter w/2 slit valves | 0.4 psig |

Minimum valve opening vacuum levels are outlined in Table 4 below.

TABLE 4

| PVC catheter w/2 slit valves | (−)11.9 psig |
| --- | --- |
| PVC catheter w/6 slit valves | (−)10.6 psig |
| SR catheter w/2 slit valves | (−)9.7 psig |
| SR catheter w/6 slit valves | (−)11.0 psig |
| SRw/S catheter w/2 slit valves | (−)2.2 psig |

It should further be mentioned that using pressure between the PVS and SRw/S catheters, once the PVC catheters opened, they generally stayed open. The SRw/S catheter closed and produced approximately the same opening pressures in repeat determinations.

The SRw/S catheters were statistically different from all of the other test groups using vacuum aspiration. The SRw/S catheter valves opened consistently and at low operating vacuum levels. The other test groups either opened at higher levels or were inconsistent in opening vacuum levels.

The SRw/S catheters also opened consistently and at low operating levels using pressure infusion. The PVC6 valve and SR 6 valve catheters opened at intermediate pressures, but not consistently. Both the PVC and SR 2 valve catheters required high operating pressures to open consistently.

The SRw/S catheters were the only test group that performed consistently and at low operating values. The SR catheters (all) opened and closed. The PVC catheters, once opened, generally stayed open.

The comparative testing indicated that the Cami catheters are unable to perform consistently and at low operating values. Once opened, the valves of the Cami catheter generally stayed open. This result is unlike the catheters of the present invention, treated with silicone oil, which performed consistently and at low operating values. The catheters of the present invention opened and closed reproducibly at high and low pressure differentials. Thus, catheters made according to Cami could not form a plurality of valves to perform as consistently or reproducibly as the catheters of the present invention. Nor could the Cami catheters form a plurality of valves and expect a primary valve to be preferably operable, with secondary valves acting as surrogates should the primary valve fail to operate, like the catheters of the present invention.

SUMMARY

In summary, the present invention permits biased infusion or aspiration of fluid through a primary valve of an intravascular catheter while providing secondary valves for infusing or aspirating fluids should the primary valve become partially or totally occluded.

From the foregoing, it will be appreciated that the present invention provides an apparatus and method for a catheter having a primary valve that is preferably operated in relation to any proximal secondary valves during infusion and flushing to minimize the remainder of infused fluids in the lumen of the catheter.

Additionally, the present invention provides an apparatus and methods for a catheter having a plurality of valves such that the valves are located so as not to destroy the structural integrity of the catheter, particularly at the distal end of the catheter.

The present invention also provides apparatus and methods for a catheter having a plurality of valves which will have the capacity for placing and using the catheter without a major deviation from currently existing standard practices.

Further, the present invention provides for apparatus and methods for a catheter having a plurality of valves wherein the plurality of valves operate at the positive and negative pressure differentials applicable in single-valve catheters.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States patent is:

1. A catheter for use in aspirating or infusing fluids to a patient, the catheter comprising:

a cannula having an outer-wall made of a biocompatible material, the cannula having a distal end and a proximal end and at least one internal lumen for transmitting liquids, the at least one internal lumen providing for two-way fluid flow between the proximal end and the distal end of the cannula such that the fluid flow is initiated by the application of a pressure differential to the fluid;

means for selectively communicating between the at least one lumen of the cannula and the exterior of the cannula, said means for selectively communicating comprising a plurality of valves, the plurality of valves being comprised of a primary valve and a secondary valve, the primary valve being constructed to operate at a lower threshold pressure differential than the secondary valve so as to be preferably operable relative to the secondary valve during aspiration or infusion, the secondary valve acting as a surrogate to the primary valve should the primary valve fail to operate.

2. A catheter for use in aspirating or infusing fluids to a patient as in claim 1, wherein the cannula is a single lumen catheter.

3. A catheter for use in aspirating or infusing fluids to a patient as in claim 1, wherein the cannula is a multi-lumen catheter.

4. A catheter for use in aspirating or infusing fluids to a patient as in claim 1, wherein at least one internal lumen has a cross-section that is transversely asymmetrical and comprises at least one corner, the corner forming part of a localized reduced thickness region in the cannular wall.

5. A catheter for use in aspirating or infusing fluids to a patent as in claim 3, wherein the plurality of valves in the multi-lumen catheter are capable of being mechanically weakened.

6. A catheter for use in aspirating or infusing fluids to a patient as in claim 3, wherein the plurality of valves in the multi-lumen catheter are capable of being mechanically weakened to different degrees by varying the lengths of the valves.

7. A catheter for use in aspirating or infusing fluids to a patient as in claim 3, wherein the plurality of valves in the multi-lumen catheter are capable of being mechanically weakened to different degrees by varying the wall thickness between that at least one lumen and the exterior of the cannula in the valve area.

8. A catheter for use in aspirating or infusing fluids to a patient as in claim 3, wherein the plurality of valves in the single lumen cannula are capable of being chemically softened.

9. A catheter as recited in claim 1, wherein each of the plurality of valves comprises a two-way valve.

10. A catheter as recited in claim 1, wherein each of the plurality of valves comprises a slit extending through the wall of the catheter, said slit having edges which abut each other to prevent fluid flow therethrough, the edges moving outwardly from one another upon the application of a positive pressure differential to the at least one lumen to infuse fluids from the at least one lumen, and the edges moving inwardly upon the application of a negative pressure differential to the at least one lumen to withdraw fluid from the at least one lumen.

11. A catheter as recited in claim 1, wherein said primary valve is located distal of said secondary valve along the length of said cannula.

12. A catheter for use in aspirating or infusing fluids to a patient, the catheter comprising:
   a single-lumen cannula having an outer-wall made of a biocompatible material, the cannula having a distal end and a proximal end and an internal lumen for transmitting liquids, the internal lumen providing for two-way fluid flow between the proximal end and the distal end of the cannula such that the fluid flow is initiated by the application of a pressure differential to the fluid;
   a plurality of multi-position valves communicating between the lumen of the cannula and the exterior of the cannula having edges which abut each other to prevent fluid flow therethrough, the edges moving outwardly from one another upon the application of a positive pressure differential to the lumen to infuse fluids from the lumen, the edges moving inwardly upon the application of a negative pressure differential to the lumen to withdraw fluid from the lumen, and wherein the material from which the cannula adjacent each valve is chemically softened with silicone oil in order to provide for the two-way operation; and
   the plurality of valves comprised of a primary valve constructed to be preferably operable during aspiration or infusion, and at least one secondary valve acting as a surrogate to the primary valve should the primary valve fail to operate.

13. A catheter for use in aspirating or infusing fluids to a patient as in claim 2, wherein the plurality of valves in the single lumen cannula are capable of being mechanically weakened.

14. A catheter for use in aspirating or infusing fluids to a patient as in claim 1, wherein the plurality of valves are three-position valves.

15. A catheter for use in aspirating or infusing fluids to a patient as in claim 2, wherein the valves have a Shore A durometer in the range from about 10 to about 45.

16. A catheter for use in aspirating or infusing fluids to a patient as in claim 2, wherein the valves have a Shore A durometer in the range from about 20 to about 35.

17. A catheter for use in aspirating or infusing fluids to a patient as in claim 2, wherein the valves have a Shore A durometer in the range from about 24 to about 31.

18. A catheter for use in aspirating or infusing fluids to a patient as in claim 1, wherein the valves are capable of operating to consistently and reproducibly open and close over long-term indwelling conditions.

19. A catheter for use in aspirating or infusing fluids to a patient as in claim 18, wherein the valves are capable of operating to consistently and reproducibly open and close at low-pressure differentials.

20. A catheter for use in aspirating or infusing fluids into a patient as in claim 19, wherein the valves are capable of operating to consistently and reproducibly open and close at push pressures in the range from about 1.5 psig to about 10.0 psig and at pull pressures in the range from about 0.3 psig to about 2.0 psig.

21. A catheter for use in aspirating or infusing fluids to a patient as in claim 3, wherein the primary valve is preferably operable to any secondary valves because the primary valve is mechanically weakened to a greater degree than any secondary valves.

22. A catheter for use in aspirating or infusing fluids to a patient as in claim 1, wherein the primary valve has a slit length in the range from about 0.300 to about 0.400 inches and the secondary valves have a slit length in the range from about 0.150 to about 0.250 inches.

23. A catheter for use in aspirating or infusing fluids to a patient as in claim 1, wherein the primary valve has a slit length in the range from about 0.330 to about 0.370 inches and the secondary valves have a slit length in the range from about 0.180 to about 0.220 inches.

24. A catheter for use in aspirating or infusing fluids to a patient as in claim 1, wherein the primary valve has a slit length in the range from about 0.340 to about 0.360 inches and the secondary valves have a slit length in the range from about 0.190 to about 0.210 inches.

25. A catheter for use in aspirating or infusing fluids to a patient, the catheter comprising:

a single-lumen cannula having an outer-wall made of a biocompatible material, the cannula having a distal end and a proximal end and an internal lumen for transmitting liquids, the internal lumen providing for two-way fluid flow between the proximal end and the distal end of the cannula such that the fluid flow is initiated by the application of a pressure differential to the fluid;

a plurality of multi-position valves communicating between the lumen of the cannula and the exterior of the cannula having edges which abut each other to prevent fluid flow therethrough, the edges moving outwardly from one another upon the application of a positive pressure differential to the lumen to infuse fluids from the lumen, the edges moving inwardly upon the application of a negative pressure differential to the lumen to withdraw fluid from the lumen; and the plurality of valves comprised of a primary valve constructed to be preferably operable during aspiration or infusion, and at least one secondary valve acting as a surrogate to the primary valve should the primary valve fail to operate, wherein the primary valve is preferably operable to any secondary valves because the primary valve is chemically softened to a greater degree than any secondary valves.

26. A catheter for use in aspirating or infusing fluids to a patient in claim 1, wherein the cannula is a long-term indwelling intravascular catheter.

27. A catheter for use in aspirating or infusing fluids to a patient as in claim 1, wherein the valves are longitudinally displaced from each other while still providing structural integrity at the distal end of the cannula for defining at least one lumen.

28. A catheter for use in aspirating or infusing fluids to a patient as in claim 1, wherein the valves are longitudinally displaced from each other so that the distal end of the proximal valve is substantially the same longitudinal distance from the distal end of cannula as the proximal end of the distal valve.

29. A catheter for use in aspirating or infusing fluids to a patient as in claim 1, wherein the valves are radially displaced from each other while still providing structural integrity at the distal end of the cannula for defining at least one lumen.

30. A catheter for use in aspirating or infusing fluids to a patient as in claim 29, wherein the valves are radially displaced from the each other in the range from about 10 to about 180 degrees.

31. A catheter for use in aspirating or infusing fluids to a patient as in claim 1, wherein the cannula has a Shore A durometer in the range from about 45 to about 70.

32. A catheter for use in aspirating or infusing fluids to a patient as in claim 1, further comprising a length of resilient tubing mounted to said cannula and extending along a relatively short distal end segment thereof, the valves being located along the short distal end segment of the catheter to which the tubing is mounted.

33. A catheter for use in aspirating or infusing fluids to a patient in claim 32, further comprising means defining an aperture in the tubing wall directly opposite and surrounding each valve, each said aperture being wider than its corresponding valve so that tubing wall portions on opposite sides of the slit overhang the opposite edges of the associated aperture.

34. A catheter for use in aspirating or infusing fluids to a patient in claim 1, wherein the cannula has a region subject to compressive forces during infusion and aspiration, the cannula having means positioned within the lumen of the cannula for site-selectively reinforcing the region of the cannula where the compressive forces are applied against the cannula.

35. A catheter for use in aspirating or infusing fluids to a patient as in claim 34, wherein the means for site-selectively reinforcing the cannula comprises an inner tubular sleeve capable of withstanding compressive forces generated by the body of a patient, said inner tubular sleeve is inserted site-selectively within the cannula.

36. A multi-lumen catheter for use in aspirating or infusing fluids to a patient, the multi-lumen catheter comprising:

a cannula having an outer-wall made of a biocompatible material, the cannula having a distal end and a proximal end and a plurality of internal lumens for transmitting liquids, the internal lumens providing for two-way fluid flow between the proximal end and the distal end of the cannula such that the fluid flow is initiated by the application of a pressure differential to the fluid;

a plurality of three-position valves communicating between each of the lumens of the cannula and the exterior of the cannula having edges which abut each other to prevent fluid flow therethrough, the edges moving outwardly from one another upon the application of a positive pressure differential to the lumens to infuse fluids from the lumens, the edges moving inwardly upon the application of a negative pressure differential to the lumen to withdraw fluid from the lumens; and the plurality of valves comprised of a primary valve and a secondary valve, the primary valve constructed to operate at a lower threshold pressure differential than the secondary valve so as to be preferably operable relative to the secondary valve during aspiration or infusion, and the secondary valve acting as a surrogate to the primary valve should the primary valve fail to operate.

37. A multi-lumen catheter for use in aspirating or infusing fluids to a patient as in claim 36, wherein the valves are capable of being mechanically weakened.

38. A multi-lumen catheter for use in aspirating or infusing fluids to a patient as in claim 36, wherein the valves are capable of being mechanically weakened to different degrees by varying the lengths of the valves.

39. A multi-lumen catheter for use in aspirating or infusing fluids to a patient as in claim 36, wherein the valves are capable of being mechanically weakened to different degrees by varying the wall thickness between the lumens and the exterior of the cannula in the valve area.

40. A multi-lumen catheter for use in aspirating or infusing fluids to a patient as in claim 36, wherein the valves are capable of operating to consistently and reproducibly open and close over long-term indwelling conditions.

41. A multi-lumen catheter for use in aspirating or infusing fluids to a patient as in claim 40, wherein the valves are capable of operating to consistently and reproducibly open and close at low pressure differentials.

42. A catheter for use in aspirating or infusing fluids into a patient as in claim 41, wherein the valves are capable of operating to consistently and reproducibly open and close at push pressures in the range from about 1.5 psig to about 10.0 psig and at pull pressures in the range from about 0.3 psig to about 2.0 psig.

43. A multi-lumen catheter for use in aspirating or infusing fluids to a patient as in claim 36, wherein each primary valve in each of the lumens is preferably operable to any second valves because the primary valve is mechanically weakened to a greater degree than any of the secondary valves.

44. A multi-lumen catheter for use in aspirating or infusing fluids to a patient as in claim 36, wherein the cannula is a long-term indwelling intravascular catheter.

45. A multi-lumen catheter for use in aspirating or infusing fluids to a patient as in claim 36, wherein the valves are longitudinally displaced from each other while still providing structural integrity at the distal end of the cannula for defining a plurality of lumens.

46. A multi-lumen catheter for use in aspirating or infusing fluids to a patient as in claim 36, wherein the valves are longitudinally displaced from each other so that the distal end of the proximal valve is substantially the same longitudinal distance from the distal end of cannula as the proximal end of the distal valve.

47. A multi-lumen catheter for use in aspirating or infusing fluids to a patient as in claim 36, wherein the valves are radially displaced from each other while still providing structural integrity at the distal end of the cannula for defining a plurality of lumens.

48. A catheter for use in aspirating or infusing fluids to a patient, the catheter comprising:
a cannula having a distal end and a proximal end and defining a tubular wall providing for fluid flow from the proximal end to the distal end, fluid being initiated by applying a pressure differential at the proximal end of the cannula; and
a plurality of multi-positioned valves placed in the wall layers of the cannula near the distal end, each of the plurality of valves enabling fluid flow through the cannula through the valve subject to the differential applied to the proximal end, each of the plurality of valves being configured to reseal such that fluid is prevented from passing through the valve when the pressure differential is terminated, the plurality of valves comprised of a primary valve and a secondary valve, the primary valve constructed to operate at a lower threshold pressure differential than the secondary valve so as to be preferably operable relative to the secondary valve during aspiration or infusion, and the secondary valve acting as a surrogate to the primary valve should the primary valve fail to operate.

49. A catheter for use in aspirating or infusing fluids to a patient as in claim 48, wherein the cannula is a single-lumen catheter.

50. A catheter for use in aspirating or infusing fluids to a patient as in claim 48, further comprising wall means defining a plurality of independently usable lumens extending substantially the entire length of the cannula, the lumen-defining wall means being internally located at the distal end, each lumen being capable of communicating with a plurality of valves.

51. A catheter for use in aspirating or infusing fluids to a patient as in claim 50, wherein the wall means define two independent lumens extending substantially the entire length of the cannula, each lumen being capable of communicating with a plurality of valves.

52. A catheter for use in aspirating or infusing fluids to a patient as in claim 49, wherein the valves are capable of being chemically softened.

53. A catheter for use in aspirating or infusing fluids to a patient as in claim 51, wherein the valves are capable of being mechanically weakened.

54. A catheter for use in aspirating or infusing fluids to a patient as in claim 51, wherein the valves are capable of being mechanically weakened to different degrees by varying the lengths of the valves.

55. A catheter for use in aspirating or infusing fluids to a patient as in claim 51, wherein the valves are capable of being mechanically weakened to different degrees by varying the wall thickness between the lumen and the exterior of the cannula in the valve area.

56. A catheter for use in aspirating or infusing fluids to a patient as in claim 48, wherein the valves are three-position, two-way valves.

57. A catheter for use in aspirating or infusing fluids to a patient, the catheter comprising:
a single-lumen cannula having a distal end and a proximal end and defining a tubular wall providing for fluid flow from the proximal end to the distal end, fluid being initiated by applying a pressure differential at the proximal end of the cannula; and
a plurality of multi-positioned valves placed in the wall layers of the cannula near the distal end, each of the plurality of valves enabling fluid flow through the cannula through the valve subject to the differential applied to the proximal end, each of the plurality of valves being configured to reseal such that fluid is prevented from passing through the valve when the pressure differential is terminated, the plurality of valves comprised of a primary valve constructed to be preferably operable during aspiration or infusion, and at least one secondary valve acting as a surrogate to the primary valve should the primary valve fail to operate, and wherein the cannula adjacent each valve is chemically softened with silicone in order to provide for the two-way, three-position operation.

58. A catheter for use in aspirating or infusing fluids to a patient as in claim 48, wherein the primary valve comprises a region of enhanced flexibility in the material from which the primary valve is comprised.

59. A catheter for use in aspirating or infusing fluids to a patient as in claim 48, wherein the primary valve comprises a relatively thin localized site in the material from which the primary valve is comprised.

60. A catheter for use in aspirating or infusing fluids to a patient as in claim 48, wherein the valves are capable of operating to consistently and reproducibly open and close over long-term indwelling conditions.

61. A catheter for use in aspirating or infusing fluids to a patient as in claim 60, wherein the valves are capable of operating to consistently and reproducibly open and close at low pressure differentials.

62. A catheter for use in aspirating or infusing fluids into a patient as in claim 61, wherein the valves are capable of operating to consistently and reproducibly open and close at push pressures in the range from about 1.5 psig to about 10.0 psig and at pull pressures in the range from about 0.3 psig to about 2.0 psig.

63. A catheter for use in aspirating or infusing fluids to a patient as in claim 51, wherein the primary valve is preferably operable to any secondary valves because the primary valve is mechanically weakened to a greater degree than any secondary valve.

64. A catheter for use in aspirating or infusing fluids to a patient, the catheter comprising:
   a cannula having a distal end and a proximal end and defining a tubular wall providing for fluid flow from the proximal end to the distal end, fluid being initiated by applying a pressure differential at the proximal end of the cannula; and
   a plurality of multi-positioned valves placed in the wall layers of the cannula near the distal end, each of the plurality of valves enabling fluid flow through the cannula through the valve subject to the differential applied to the proximal end, each of the plurality of valves being configured to reseal such that fluid is prevented from passing through the valve when the pressure differential is terminated, the plurality of valves comprised of a primary valve constructed to be preferably operable during aspiration or infusion, and at least one secondary valve acting as a surrogate to the primary valve should the primary valve fail to operate, and wherein the primary valve is preferably operable to any secondary valves because the primary valve is chemically softened to a greater degree than any secondary valve.

65. A catheter for use in aspirating or infusing fluids to a patient as in claim 48, wherein the cannula is a long-term indwelling intravascular catheter.

66. A catheter for use in aspirating or infusing fluids to a patient as in claim 48, wherein the valves are longitudinally displaced from each other while still providing structural integrity at the distal end of the cannula.

67. A catheter for use in aspirating or infusing fluids to a patient as in claim 48, wherein the valves are longitudinally displaced from each other so that the distal end of the proximal valve is substantially the same longitudinal distance from the distal end of the cannula as the proximal end of the distal valve.

68. A catheter for use in aspirating or infusing fluids to a patient as in claim 48, wherein the valves are radially displaced from each other while still providing structural integrity at the distal end of the cannula.

69. A catheter for use in aspirating or infusing fluids to a patient as in claim 49, wherein the valves are radially displaced from each other in the range from about 10 to about 180 degrees.

70. A catheter for use in aspirating or infusing fluids to a patient as in claim 46, wherein the valves have a Shore A durometer in the range from about 45 to about 70 prior to being softened.

71. A catheter for use in aspirating or infusing fluids to a patient as in claim 48, further comprising a length of resilient tubing mounted to said cannula and extending along a relatively short distal end segment thereof, the valves being located along the short distal end segment of the cannula to which the tubing is mounted.

72. A catheter for use in aspirating or infusing fluids to a patient as in claim 71, further comprising means defining an aperture in the tubing wall directly opposite and surrounding each valve, each said aperture being wider than its corresponding valve so that tubing wall portions on opposite sides of the slit overhand the opposite edges of the associated aperture.

73. A catheter for use in aspirating or infusing fluids to a patient as in claim 48, wherein the cannula has a region subject to compressive forces during infusion and aspiration, the cannula having means positioned within the lumen of the cannula for site-selectively reinforcing the region of the cannula where the compressive forces are applied against the cannula.

74. A catheter for use in aspirating or infusing fluids to a patient as in claim 73, wherein the means for site-selectively reinforcing the cannula comprises an inner tubular sleeve capable of withstanding compressive forces generated by the body of a patient, said inner tubular sleeve being positioned site-selectively within the cannula.

75. An intravascular catheter for infusing and aspirating fluids in the area surrounding the catheter, the catheter comprising:
   a close-ended single lumen catheter having a distal end and a proximal end and defining a tubular wall which allows an even flow through the lumen of the catheter, the even flow being initiated when a pressure differential is applied to said catheter; and
   two valves in the walls of the catheter comprised of a material for resealing when the pressure differential is withdrawn, the catheter maintaining a predetermined degree of catheter-tip rigidity to maintain structural integrity while the valves consistently and reproducibly open and close to enable infusion and aspiration, the valves comprised of a single, normally closed, linearly extending slit extending through the catheter wall, one of the two slits being radially and longitudinally displaced from the other slit while still providing structural integrity at the distal end of the catheter, the first of the two valves being a primary valve constructed to be preferably operable during aspiration or infusion, the second of the two valves acting as a surrogate to the primary valve should the primary valve fail to operate, the primary valve being treated to operate at a lower threshold pressure differential relative to the secondary valve so as to be preferably operable to the secondary valve.

76. An intravascular catheter for infusing and aspirating fluids in the area surrounding the catheter as in claim 75, wherein one of the two valves is radially displaced from the other valve in the range from about 10 to about 180 degrees.

77. An intravascular catheter for infusing and aspirating fluids in the area surrounding the catheter as in claim 75, wherein one of the two valves is longitudinally displaced from the other valve so that the distal end of the proximal valve us substantially the same longitudinal distance from the distal end of the catheter as the proximal end of the distal valve.

78. An intravascular catheter for infusing and aspirating fluids in the area surrounding the catheter as in claim 75, wherein said valves have a Shore A durometer in the range from about 10 to about 45.

79. An intravascular catheter for infusing and aspirating fluids in the area surrounding the catheter as in claim 75, wherein said valves have a Shore A durometer in the range from about 20 to about 35.

80. An intravascular catheter for infusing and aspirating fluids in the area surrounding the catheter as in claim 75, wherein said valves have a Shore A durometer in the range from about 24 to about 31.

81. An intravascular catheter for infusing and aspirating fluids in the area surround the catheter as in claim 75, wherein the valves are capable of being mechanically weakened to different degrees by varying the lengths of the valves.

82. An intravascular catheter for infusing and aspirating fluids in the area surround the catheter as in claim 75, wherein the valves are capable of being mechanically weakened to different degrees by varying the wall thickness between the lumen and the exterior of the catheter in the valve area.

83. An intravascular catheter for infusing and aspirating fluids in the area surrounding the catheter as in claim 75, wherein the valves are capable of being chemically softened.

84. An intravascular catheter for infusing and aspirating fluids in the area surrounding the catheter, the catheter comprising:

a close-ended single lumen catheter having a distal end and a proximal end and defining a tubular wall which allows an even flow through the lumen of the catheter, the even flow being initiated when a pressure differential is applied to said catheter; and two valves in the walls of the catheter comprised of a material for resealing when the pressure differential is withdrawn, the catheter maintaining a predetermined degree of catheter-tip rigidity to maintain structural integrity while the valves consistently and reproducibly open and close to enable infusion and aspiration, the valves comprised of a single, normally closed, linearly extending slit extending through the catheter wall, one of the two slits being radially and longitudinally displaced from the other slit while still providing structural integrity at the distal end of the catheter, the first of the two valves being a primary valve constructed to be preferably operable during aspiration or infusion, the second of the two valves acting as a surrogate to the primary valve should the primary valve fail to operate, the primary valve being treated to be preferably operable to the secondary valve, and wherein the valves are chemically softened with silicone oil.

85. An intravascular catheter for infusing and aspirating fluids in the area surrounding the catheter as in claim 75, wherein the valves are capable of operating to consistently and reproducibly open and close at low pressure differentials.

86. An intravascular catheter for infusing and aspirating fluids in the area surrounding the catheter as in claim 75, wherein the primary valve is preferably operable to any secondary valve because the primary valve is mechanically weakened to a greater degree than any secondary valve.

87. An intravascular catheter for infusing and aspirating fluids in the area surround the catheter as in claim 75, wherein the primary valve has a slit length in the range from about 0.300 to about 0.400 inches and the secondary valves have a slit length in the range from about 0.150 to about 0.250 inches.

88. An intravascular catheter for infusing and aspirating fluids in the area surround the catheter as in claim 75, wherein the primary valve has a slit length in the range from about 0.330 to about 0.370 inches and the secondary valves have a slit length in the range from about 0.180 to about 0.220 inches.

89. An intravascular catheter for infusing and aspirating fluids in the area surround the catheter as in claim 75, wherein the primary valve has a slit length in the range from about 0.360 inches and the secondary valves have a slit length in the range from about 0.190 to about 0.210 inches.

90. An intravascular catheter for infusing and aspirating fluids in the area surrounding the catheter, the catheter comprising:

a close-ended single lumen catheter having a distal end and a proximal end and defining a tubular wall which allows an even flow through the lumen of the catheter, the even flow being initiated when a pressure differential is applied to said catheter; and two valves in the walls of the catheter comprised of a material for resealing when the pressure differential is withdrawn, the catheter maintaining a predetermined degree of catheter-tip rigidity to maintain structural integrity while the valves consistently and reproducibly open and close to enable infusion and aspiration, the valves comprised of a single, normally closed, linearly extending slit extending through the catheter wall, one of the two slits being radially and longitudinally displaced from the other slit while still providing structural integrity at the distal end of the catheter, the first of the two valves being a primary valve constructed to be preferably operable during aspiration or infusion, the second of the two valves acting as a surrogate to the primary valve should the primary valve fail to operate, the primary valve being treated to be preferably operable to the secondary valve, and wherein the primary valve is preferable operable to any secondary valve because the primary valve is chemically softened to a greater degree than any secondary valve.

91. An intravascular catheter for infusing and aspirating fluids in the area surrounding the catheter as in claim 75, wherein the catheter has a Shore A durometer in the range from about 45 to about 70.

92. An intravascular catheter for infusing and aspirating fluids in the area surrounding the catheter as in claim 75, further comprising a length of resilient tubing mounted to said catheter and extending along a relatively short distal end segment thereof, the valves being located along the short distal end segment of the catheter to which the tubing is mounted.

93. An intravascular catheter for infusing and aspirating fluids in the area surrounding the catheter as in claim 92, further comprising means defining an aperture in the tubing wall directly opposite and surrounding each valve, each said aperture being wider than its corresponding valve so that tubing wall portions on opposite sides of the slit overhang the opposite edges of the associated aperture.

94. An intravascular catheter for infusing and aspirating fluids in the area surrounding the catheter as in claim 75, wherein the catheter has region subject to compressive forces during infusion and aspiration, the catheter having means positioned within the lumen of the catheter for site-selectively reinforcing the region of the catheter where the compressive forces are applied against the catheter.

95. An intravascular catheter for infusing and aspirating fluids in the area surrounding the catheter as in claim 94, wherein the means for site-selectively reinforcing the catheter comprises an inner tubular sleeve capable of withstanding compressive forces generated by the body of a patient, said inner tubular sleeve being positioned site-selectively within the catheter.

* * * * *

UNITED STATES PATENT AND TRADEMARK OFFICE
CERTIFICATE OF CORRECTION

PATENT NO. : 5,147,332                          Page 1 of 2

DATED : September 15, 1992

INVENTOR(S) : H. ROBERT MOOREHEAD

It is certified that error appears in the above-identified patent and that said Letters Patent is hereby corrected as shown below:

Column 3, line 1, after "from" insert --its implanted position. Although the current state of--
    Column 6, line 67, after "proximal end" insert --20--
    Column 7, line 55, "value" should be --valve--
    Column 8, line 43, "exist" should be --exists--
    Column 14, line 52, "a ct" should be --act--
    Column 16, line 37, after "12" insert --.--
    Column 16, line 48, after "made" insert --to form distal valve 18 is greater than the length of the slit--
    Column 17, line 5, "or" should be --of--
    Column 17, line 17, delete "include"
    Column 19, line 67, "ARw/s" should be --SRw/S--
    Column 20, line 12, "silicon" should be --silicone--
    Column 20, line 16, "silicon" should be --silicone--
    Column 20, line 18, "silicon" should be --silicone--
    Column 23, line 18, "cannular" should be --cannula--
    Column 29, line 47, "as in claim 46," should be --as in claim 52--
    Column 30, line 47, "us" should be --is--
    Column 31, line 49, "surround" should be --surrounding--
    Column 31, line 55, "surround" should be --surrounding--
    Column 31, line 61, "surround" should be --surrounding--

UNITED STATES PATENT AND TRADEMARK OFFICE
CERTIFICATE OF CORRECTION

PATENT NO. : 5,147,332

DATED : September 15, 1992

INVENTOR(S) : H. ROBERT MOOREHEAD

It is certified that error appears in the above-indentified patent and that said Letters Patent is hereby corrected as shown below:

Column 32, line 52, after "has" insert ---a---

Signed and Sealed this

Fourteenth Day of December, 1993

*Attest:*

BRUCE LEHMAN

*Attesting Officer*   Commissioner of Patents and Trademarks